(12) United States Patent
Harris et al.

(10) Patent No.: US 8,821,941 B2
(45) Date of Patent: *Sep. 2, 2014

(54) HAIR REMOVAL WITH NANOPARTICLES

(71) Applicant: Sienna Labs, Inc., San Diego, CA (US)

(72) Inventors: Todd James Harris, San Celemente, CA (US); Alice Ann Chen Kim, San Francisco, CA (US)

(73) Assignee: Sienna Labs, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/020,481

(22) Filed: Sep. 6, 2013

(65) Prior Publication Data

US 2014/0005593 A1 Jan. 2, 2014

Related U.S. Application Data

(63) Continuation of application No. 13/219,514, filed on Aug. 26, 2011.

(60) Provisional application No. 61/402,305, filed on Aug. 27, 2010, provisional application No. 61/422,612, filed on Dec. 13, 2010, provisional application No. 61/516,308, filed on Apr. 1, 2011.

(51) Int. Cl.
| | | |
|---|---|---|
| *A61N 5/06* | (2006.01) | |
| *A61B 18/20* | (2006.01) | |
| *A61B 17/50* | (2006.01) | |
| *A61K 8/02* | (2006.01) | |
| *A61K 8/29* | (2006.01) | |
| *A61Q 9/04* | (2006.01) | |
| *A61Q 19/06* | (2006.01) | |
| *B82Y 5/00* | (2011.01) | |
| *A61Q 19/08* | (2006.01) | |
| *A61K 9/00* | (2006.01) | |
| *A61K 9/51* | (2006.01) | |

(52) U.S. Cl.
CPC ............ *A61N 5/0616* (2013.01); *A61B 18/203* (2013.01); *A61K 8/0283* (2013.01); *A61K 8/0245* (2013.01); *A61K 2800/81* (2013.01); *A61Q 19/06* (2013.01); *B82Y 5/00* (2013.01); *A61K 2800/624* (2013.01); *A61Q 19/08* (2013.01); *A61K 2800/413* (2013.01); *A61K 9/0009* (2013.01); *A61K 8/29* (2013.01); *A61K 2800/621* (2013.01); *A61K 9/5115* (2013.01); *A61N 5/0617* (2013.01); *A61Q 9/04* (2013.01); *A61N 5/062* (2013.01); *A61B 17/50* (2013.01); *A61K 9/0014* (2013.01)
USPC ........................... 424/489; 424/400; 424/401

(58) Field of Classification Search
USPC ........................................................ 424/489
See application file for complete search history.

(56) References Cited

U.S. PATENT DOCUMENTS

| | | |
|---|---|---|
| 5,226,907 A | 7/1993 | Tankovich |
| 5,409,797 A | 4/1995 | Hosoi et al. |
| 5,423,803 A | 6/1995 | Tankovich et al. |
| 5,647,866 A | 7/1997 | Zains et al. |
| 5,752,949 A | 5/1998 | Tankovich et al. |
| 5,817,089 A | 10/1998 | Tankovich et al. |
| 5,925,035 A | 7/1999 | Tankovich |
| 6,036,684 A | 3/2000 | Tankovich et al. |
| 6,050,990 A | 4/2000 | Tankovich et al. |
| 6,063,074 A | 5/2000 | Tankovich |
| 6,147,982 A | 11/2000 | Sourour et al. |
| 6,152,917 A | 11/2000 | Tankovich |
| 6,168,590 B1 | 1/2001 | Neev |
| 6,183,773 B1 | 2/2001 | Anderson |
| 6,267,771 B1 | 7/2001 | Tankovich et al. |
| 6,344,272 B1 | 2/2002 | Oldenburg et al. |
| 6,365,145 B1 | 4/2002 | Ben-Hur et al. |
| 6,428,811 B1 | 8/2002 | West et al. |
| 6,530,944 B2 | 3/2003 | West et al. |
| 6,600,951 B1 | 7/2003 | Anderson |
| 6,663,658 B1 | 12/2003 | Kollias et al. |
| 6,676,655 B2 | 1/2004 | McDaniel |
| 6,685,730 B2 | 2/2004 | West et al. |
| 6,685,927 B2 * | 2/2004 | Sumian et al. .................. 424/73 |
| 6,821,509 B2 | 11/2004 | Soane et al. |
| 6,897,238 B2 | 5/2005 | Anderson |
| 7,018,396 B2 | 3/2006 | Sierra et al. |
| 7,131,446 B2 | 11/2006 | Tang et al. |
| 7,201,765 B2 | 4/2007 | McDaniel |
| 7,270,721 B2 | 9/2007 | Hilfenhaus et al. |
| 7,494,503 B2 | 2/2009 | McDaniel |
| 7,648,595 B2 | 1/2010 | Jin et al. |

(Continued)

FOREIGN PATENT DOCUMENTS

| | | |
|---|---|---|
| EP | 0 601 130 B1 | 8/1998 |
| EP | 0 712 322 B1 | 4/1999 |

(Continued)

OTHER PUBLICATIONS

Ammad et al. "An assessment of the efficacy of blue light phototherapy in the treatment of acne vulgaris." *J. Cosmet Dermatol*, 2008, 7: 180-188.
Choudhary and Elsaie, M.L. "Photodynamic therapy in dermatology: a review." *Lasers Med Sci.*, 2009, 24:971-980.
Donnelly et al. "Photosensitiser delivery for photodynamic therapy. Part 1: Topical carrier platforms." *Expert Opin Drug Deliv.* 2008, 5:757-766.
Gollnick et al. "Can we define acne as a chronic disease? If so, how and when?" *Am J Clin Dermatol*, 2008, 9:279-284.
Grachtchouk et al. "Basal cell carcinomas in mice arise from hair follicle stem cells and multiple epithelial progenitor populations." *J Clin Invest*, 2011, 121: 1768-1781.
Grams et al. "Permeant lipophilicity and vehicle composition influence accumulation of dyes in hair follicles of human skin," *Eur J Pharm Sci*; 2003, 18:329-336.

(Continued)

*Primary Examiner* — Abigail Fisher
*Assistant Examiner* — Luke Karpinski
(74) *Attorney, Agent, or Firm* — Knobbe, Martens, Olson & Bear, LLP

(57) ABSTRACT

Provided are nanoparticles and formulations which are useful for cosmetic, diagnostic and therapeutic applications to mammals such as humans.

20 Claims, 14 Drawing Sheets

(56) References Cited

U.S. PATENT DOCUMENTS

| | | | |
|---|---|---|---|
| 7,659,301 | B2 | 2/2010 | Anderson |
| 7,704,754 | B2 | 4/2010 | Malak |
| 7,776,130 | B2 | 8/2010 | Mirkin et al. |
| 8,178,202 | B2 | 5/2012 | Halas et al. |
| 8,268,332 | B2 | 9/2012 | Manstein |
| 2001/0002275 | A1 | 5/2001 | Oldenburg et al. |
| 2002/0103517 | A1 | 8/2002 | West et al. |
| 2002/0192298 | A1 | 12/2002 | Burrell et al. |
| 2003/0072728 | A1 | 4/2003 | Soane et al. |
| 2003/0099718 | A1 | 5/2003 | Burrell et al. |
| 2004/0006328 | A1* | 1/2004 | Anderson ............ 604/501 |
| 2005/0175649 | A1 | 8/2005 | Disalvo et al. |
| 2005/0203495 | A1 | 9/2005 | Malak |
| 2005/0229334 | A1 | 10/2005 | Huang et al. |
| 2007/0032781 | A1 | 2/2007 | Henry et al. |
| 2007/0104605 | A1 | 5/2007 | Hampden-Smith et al. |
| 2007/0158611 | A1 | 7/2007 | Oldenburg |
| 2007/0208400 | A1 | 9/2007 | Nadkarni et al. |
| 2008/0241262 | A1* | 10/2008 | Lee et al. ............ 424/490 |
| 2009/0123509 | A1 | 5/2009 | Berkland et al. |
| 2009/0246142 | A1 | 10/2009 | Bhatia et al. |
| 2010/0002282 | A1 | 1/2010 | Agrawal et al. |
| 2010/0016783 | A1 | 1/2010 | Bourke, Jr. et al. |
| 2010/0055138 | A1 | 3/2010 | Margulies |
| 2010/0057068 | A1 | 3/2010 | Lee |
| 2010/0143431 | A1 | 6/2010 | Landau et al. |
| 2010/0174223 | A1 | 7/2010 | Sakamoto et al. |
| 2010/0204686 | A1 | 8/2010 | Yarolslavksy et al. |
| 2010/0224026 | A1 | 9/2010 | Fournet et al. |
| 2010/0291224 | A1 | 11/2010 | Tong et al. |
| 2010/0298758 | A1 | 11/2010 | Christiansen et al. |
| 2011/0034855 | A1 | 2/2011 | Esenaliev |
| 2011/0052672 | A1 | 3/2011 | Krishnan et al. |
| 2011/0091572 | A1 | 4/2011 | Davidson |
| 2011/0159291 | A1 | 6/2011 | Sun et al. |
| 2011/0240556 | A1 | 10/2011 | Hoek et al. |
| 2011/0288234 | A1 | 11/2011 | Pandey |
| 2012/0059307 | A1 | 3/2012 | Harris et al. |
| 2012/0101007 | A1 | 4/2012 | Ahern et al. |
| 2012/0141380 | A1 | 6/2012 | Margel et al. |
| 2013/0315999 | A1 | 11/2013 | Paithankar et al. |
| 2013/0323305 | A1 | 12/2013 | Paithankar et al. |

FOREIGN PATENT DOCUMENTS

| | | |
|---|---|---|
| EP | 0925807 A1 | 6/1999 |
| EP | 0860123 B1 | 1/2002 |
| WO | WO 9533518 | 12/1995 |
| WO | WO 96/20698 | 7/1996 |
| WO | WO 9641579 | 12/1996 |
| WO | WO 9700098 | 1/1997 |
| WO | WO 99/46351 | 9/1999 |
| WO | WO 00/02590 | 1/2000 |
| WO | WO 0040266 | 7/2000 |
| WO | WO 01/05586 | 1/2001 |
| WO | WO 01/06257 | 1/2001 |
| WO | WO 01/58458 | 8/2001 |
| WO | WO 02/085385 | 10/2002 |
| WO | WO 03/026481 | 4/2003 |
| WO | WO 2004058352 | 7/2004 |
| WO | WO 2004/086044 | 10/2004 |
| WO | WO 2005/092286 | 10/2005 |
| WO | WO 2008/106966 | 9/2008 |
| WO | WO 2009/117124 | 9/2009 |
| WO | WO 2010/073260 | 7/2010 |
| WO | WO 2010/116345 | 10/2010 |
| WO | WO 2011/031871 | 3/2011 |
| WO | WO 2011/116963 | 9/2011 |
| WO | WO 2012/027728 | 3/2012 |
| WO | WO 2012/059944 | 5/2012 |
| WO | WO 2013/158278 | 10/2013 |

OTHER PUBLICATIONS

Hongcharu et al. "Topical ALA-photodynamic therapy for the treatment of acne vulgaris." *J Invest Dermatol*, 2000, 115:183-192.

Huang et al. Microemulsification of triglyceride sebum and the role of interfacial structure on bicontinuous phase behavior.: *Langmuir*, 2004, 20:3559-3563.

Knorr et al. "Follicular transport route-research progress and future perspectives." *Eur J Pharm Biopharm*, 2009, 71:173-180.

Lademann et al. "Nanoparticles—an efficient carrier for drug delivery into the hair follicles." *Eur J Pharm Biopharm*, 2007, 66:159-164.

Mallon et al. "The quality of life in acne: a comparison with general medical conditions using generic questionnaires." *Br J Dermatol*, 1999, 140:672-676.

Meidan, V.M. "Methods for quantifying intrafollicular drug delivery: a critical appraisal." *Expert Opin Drug Deliv*, 2010, 7:1095-1108.

Mitragotri et al. "Synergistic effect of low-frequency ultrasound and sodium lauryl sulfate on transdermal transport." *J Pharm Sci*; 2000, 89:892-900.

Mortensen et al. "In vivo skin penetration of quantum dot nanoparticles in the murine model: the effect of UVR." *Nano Lett*, 2008, 8:2779-2787.

Nanni, C.A. and Alster, T.S. (1997). "Optimizing treatment parameters for hair removal using a topical carbon-based solution and 1064-nm Q-switched neodymium: YAG laser energy." *Arch Dermatol*, 1997, 133:1546-1549.

PCT/US2011/049464 International Search Report mailed Apr. 24, 2012.

Polat et al. "Ultrasound-mediated transdermal drug delivery: Mechanisms, scope, and emerging trends." *J Control Release*, 2011, 152:330-348.

Rogers et al. "Hair removal using topical suspension-assisted Q-switched Nd:YAG and long-pulsed alexandrite lasers: A comparative study." *Dermatol Surg*, 1999, 25:844-844; discussion 848-850.

Sakamoto et al. "Photodynamic therapy for acne vulgaris: A critical review from basics to clinical practice: Part 1, Acne Vulgaris: When and why consider photodynamic therapy?" *Journal of the American Academy of Dermatology*, 2010, 63:183-193.

Sakamoto et al. "Photodynamic therapy for acne vulgaris: A critical review from basics to clinical practice: Part II. Understanding parameters for acne treatment with photodynamic therapy." *Journal of the Academy of Dermatology*, 2010, 63:195-211.

Sellheyer, K. "Basal cell carcinoma: cell of origin, cancer stem cell hypothesis and stem cell markers." *Br J Dermatol*, 2011, 164:696-711.

Sellheyer, K. (2007). "Mechanisms of laser hair removal: could persistent photoepilation induce vitiligo or defects in wound repair?" *Dermatol Surg*, 2007, 33:055-1065.

Shershen et al. "Temperature-Sensitive Polymer-Nanoshell Composites for Photothermally Modulated Drug Delivery" *Journal of Biomedical Materials Research;* vol. 51, Issue 3, pp. 293-298 (Jun. 28, 2000).

West et al. "Applications of Nanotechnology to Biotechnology" *Current Opinion in Biotechnology* 2000, 11:215-217; Published Apr. 1, 2000.

Wong, S.Y., and Reiter, J.F. "Wounding mobilizes hair follicle stem cells to form tumors." *Proc Natl Acad Sci USA*, 2011, 108:4093-4098.

Zhao, W., and Karp, J.M. "Tumour targeting: Nanoantennas heat up." *Nat Mater*, 2009, 8:453-454.

He, et al "The evidence for synthesis of truncated silver nanoplates in the presence of CTAB." Materials Characterization, 59, 380-384. (Publshed 2008).

Aherne, et al. "Optical Properties and Growth Aspects of Silver Nanoprisms Produced by Highly Reproducible and Rapid Synthesis at Room Temperature." Advanced Materials, Adv. Funct. Mater. Jul. 9, 2008, v18, 2005-2016.

Charles et al. "Versatile Solution Phase Triangular Silver Nanoplats for Highly Sensitive Plasmon Resonance Sensing" American Chemical Society NANO, v4, No. 1 p. 55-64, Dec. 23, 2009.

Chen et al. "Controlling 2-dimensional growth of silver nanoplates." Self-Assembled Nanostructured Materials Symposium. Mat. Res. Soc. Symp. Proc. vol. 775, 343-348{xiii+394. (2003).

Chen et al. "Silver nanodisks: Synthesis, characterization, and self-assembly." J. Phys. Chem. B, vol. 106, No. 42, 2002 10777-10781. (Published Sep. 21, 2002).

(56) References Cited

OTHER PUBLICATIONS

Chen, et al. "Silver nanoplates: Size control in two dimensions and formation mechanisms." J. Phys. Chem. B 2004, 108, 5500-5506 Journal of Physical Chemistry B, 108, 5500-5506. (Published Apr. 14, 2004).

Chen, et al. "Synthesis and characterization of truncated triangular silver nanoplates." Nano Letters, 2002, 2 (9), 1003-1007. (Published Jul. 26, 2002).

Dierickx, et al. "Photodynamic Therapy for Nevus Sebaceus With Topical d-Aminolevulinic Acid", Arch Dermatol, vol. 135, Jun. 1993, pp. 637-640.

Divaris, et al. "Phototoxic Damage to Sebaceous Glands and Hair Follicles of Mice After Systemic Administration of 5-Aminolevulinic Acid Correlates with Localized Protoporphyrin IX Florescence", American Journal of Pathology, vol. 136, No. 4, Apr. 1990, pp. 891-897.

Hao E. K., et al. "Synthesis of Silver Nanodisks using Polystyrene Mesospheres as Templates." J Am Chem Soc, 124, 15182-15183. (Published Nov. 22, 2002).

Hao E., et al. "Synthesis and optical properties of anisotropic metal nanoparticles." Journal of Fluorescence, vol. 14, No. 4, Jul. 2004, 331-341. (Published Jul. 2004).

He et al. "Surface Plasmon Resonances of Silver Triange Nanoplates: Graphic Assignments of Resonance Modes and Linear Fittings of Resonance Peaks" J. Phys. Chem. B 2005, 109, 17503-17511 (Published Aug. 20, 2005).

He, et al. "The evidence for synthesis of truncated silver nanoplates in the presence of CTAB." Materials Characterization, 59, 380-384. (Publshed 2008).

Hongcharu, et al. "Topical ALA-Photodynamic Therapy for the Treatment of Acne Vulgaris", Journal of Invest. Dermatology, vol. 115, No. 2, Aug. 2000, pp. 1-10.

Jiang et al. "A self-seeding coreduction method for shape control of silver nanoplates" Nanotechnology 17 (2006) 4929-4935 (Published Sep. 11, 2006).

Jin et al. "Photoinduced Conversion of Silver Nanospheres to Nanoprisms." Science, v 294, 1901-1903. (Published Nov. 30, 2001).

Jin, et al. "Controlling anisotropic nanoparticle growth through plasmon excitation." Nature, v. 425, 487-490 (Published Oct. 2, 2003).

Kjeldstad, et al. "Changes in Polyphosphate Composition and Localization in Propionibacterium Acnes After Near-Ultraviolet Irradiation", Canadian Journal of Microbiology, vol. 37, No. 7, Jul. 1991, 562-567 (Abstract, 1 Page).

Koenig, et al. "Photodynamic-Induced Inactivation of Propionibacterium Acnes", SPIE Proceedings, SPIE-Int. Soc. Opt. Eng., 106-110, vol. 3247, Jan. 1998 (Abstract, 3 Pages).

Konig, et al. "Photodynamic Activity of Methylene Blue", Aktuelle Dermatol, vol. 19, 1993, pp. 195-198.

Konig, et al. "Photodynamically Induced Inactivation of Propionibacterium Acnes Using the Photosensitizer Methylene Blue and Red Light", Dermatologische Monatsschrift (Dematol Monatsschr), vol. 178, Apr. 1992, pp. 297-300.

Le Guevel, et al. "Synthesis, Stabilization, and Functionalization of Silver Nanoplates for Biosensor Applications." J Phys Chem C, 113, 16380-16386. (Published Aug. 21, 2009).

Lloyd, et al. "Selective Photothermolysis of the Sebaceous Glands for Acne Treatment", Lasers in Surgery and Medicine, vol. 31, 2002, pp. 115-120.

Metraux, G. S. M. et al "Rapid Thermal Synthesis of Silver Nanoprisms with Chemically Tailorable Thickness." Advanced Materials, 2005, 17, No. 4, 412-415. (Published Feb. 23, 2005).

Mills, et al. "Ultraviolet Phototherapy and Photochemotherapy of Acne Vulgaris", Arch Dematol, vol. 114, No. 2, Feb. 1978 (Abstract, 2 pages).

Mutzhas, et al. "A New Apparatus with High Radiation Energy Between 320-460 nm: Physical Description and Dermatological Applications", The Journal of Investigative Dermatology, vol. 76, No. 1, Jan. 1981, pp. 42-47.

Pento, et al. "Delta-Aminolevulinic Acid", Drugs of the Future, vol. 22, No. 1, 1997, pp. 11-17.

Phillips, et al. "Medical Progress: Recent Advances in Dermatology", New England Journal of Medicine, vol. 326, No. 3, Jan. 1992, pp. 1-9 (167-176).

Schultz, et al. "The Chemorheology of Poly(vinyl alcohol)-Borate Gels." Macromolecules, vol. 2, No. 3, 281-285. (Published May-Jun. 1969).

Wainwright, Mark "Non-Porphyrin Photosensitizers in Biomedicine", Chemical Society Reviews, 1996, pp. 351-359.

Xiong, et al. "Synthesis of silver nanoplates at high yields by slowing down the polyol reduction of silver nitrate with polyacrylamide." Journal of Materials Chemistry, 17, 2600-2602. (Published May 17, 2007).

Xue, et al. "pH-Switchable Silver Nanoprism Growth Pathways." Angew. Chem. Int. Ed., 46, 2036-2038. (Published Feb. 13, 2007).

* cited by examiner

A. Topical formulation for hair removal

B. Topical formulation for acne treatment 1064 nm Laser Pulse
20 J/cm², 55ms 810 nm Laser Pulse
20 J/cm², 30 ms

Epidermal     Dermal (870 μm deep)

plane 1    plane 2

HAIR REMOVAL WITH NANOPARTICLES

CROSS REFERENCE AND INCORPORATION BY REFERENCE TO ANY PRIORITY APPLICATIONS

This application is a continuation of U.S. patent application Ser. No. 13/219,514 filed Aug. 26, 2011, which claims the benefit or priority under 35 U.S.C. §119(e) of U.S. Provisional Application Nos. 61/402,305 filed Aug. 27, 2010; 61/422,612 filed Dec. 13, 2010, and 61/516,308 filed Apr. 1, 2011; each of which is hereby incorporated by reference in its entirety. Any and all applications for which a foreign or domestic priority claim is identified in the Application Data Sheet as filed with the present application are hereby incorporated by reference under 37 CFR 1.57.

PARTIES OF JOINT RESEARCH AGREEMENT

The invention described herein was created subject to a Joint Research Agreement between Sienna Labs, Inc. and Nanocomposix, Inc.

BACKGROUND

1. Field of the Invention

The field of the invention is nanoparticles and/or photoactive compounds for use in cosmetic, diagnostic and/or therapeutic procedures.

2. Description of the Related Art

Laser treatments of the skin are widely known and have been highly touted for therapeutic and cosmetic utility. Therapeutically, potential uses for laser skin therapy include laser ablation of cancerous cells in cancer patients and laser ablation of damaged tissue in burn victims. Cosmetic applications for laser skin therapy are much more numerous, and include hair removal/reduction, treatment of dyschromia, shrinking of the skin following operations such as liposuction, acne treatment, chemical or physical abrasion of unwanted markings on the skin, surgical treatments including nose reduction and face- and neck-lifts, and other aesthetic skin remodeling purposes.

SUMMARY

Despite the promise of laser therapy for skin therapeutics and cosmetics, current laser procedures have limited efficacy, requiring prohibitive numbers of repeated treatments and driving increased costs. Suboptimal laser treatments also have limited specificity, resulting in debilitating clinical side effects, such as non-specific skin damage, skin irritation and scarring.

Light-based hair removal systems suffer from particularly low rates of efficacy at removing light hair (vellus, blonde, gray, red hair). Multiple (even 6 or more) treatments are insufficient to achieve a therapeutic result in blonde-gray- or red-haired patients, even with the use of topically applied chromophores such as carbon. In addition to light hair removal, thermoablative technology has untapped potential in the fields of wound healing, tissue remodeling, vascular repair, and acne treatment.

Acne vulgaris results from obstruction of the pilosebaceous unit, consisting of the hair shaft, hair follicle, sebaceous gland and erector pili muscle, which leads to accumulation of sebum oil produced from the sebaceous gland and the subsequent colonization of bacteria within the follicle. Microcomedones formed as a result of accumulated sebum progress to non-inflamed skin blemishes (white/blackheads), or to skin blemishes which recruit inflammatory cells and lead to the formation of papules, nodules and pus-filled cysts. The sequelae of untreated acne vulgaris often include hyperpigmentation, scarring and disfiguration, as well as significant psychological distress. Therefore, acne treatments seek broadly to reduce the accumulation of sebum and microorganisms within follicles and the sebaceous gland.

Methods involving light and lasers are promising for the treatment skin disorders, but are still insufficiently effective. Ultraviolet (UV)/blue light is approved by the FDA for the treatment of mild to moderate acne only, due to its anti-inflammatory effects mediated on skin cells (keratinocytes), potentially through the action of endogenous porphyrin photosensitizers within follicles. Exogenous porphyrin precursors such as 5-aminoluveulinic acid (5-ALA) have been formulated for topical or oral delivery and shown to accumulate within sebaceous follicles, absorb photons from red light exposure and form reactive oxygen species that directly damage cellular membranes and proteins. This procedure combining porphyrin application and high intensity red light, termed 'photodynamic therapy', has been demonstrated to reduce sebum production and acne by 50% for 20 weeks post-irradiation. However, high intensity energies (50-150 $J/cm^2$) are required to damage sebaceous gland skin structures, and transdermal porphyrin penetration leads to off-target side-effects which include sensitivity to light, pain, inflammation, hyper/hypo-pigmentation, and permanent scarring.

For laser therapy to achieve its full utility in the treatment of human skin disorders, methods to locally induce photodestruction in skin structures without affecting surrounding tissues must be achieved.

Provided herein, in certain embodiments, are new compositions and methods useful in the targeted thermomodulation of target cell populations and target tissues, for the purposes of cosmetic treatments and the treatment and prevention of chronic and acute diseases and disorders.

In one aspect, described herein are compositions of matter. For example, in one embodiment, provided is a composition comprising a cosmetically acceptable carrier and a plurality of plasmonic nanoparticles in an amount effective to induce thermomodulation in a target tissue region with which the composition is topically contacted.

In some embodiments, the composition comprises plasmonic nanoparticles that are activated by exposure to energy delivered from a nonlinear excitation surface plasmon resonance source to the target tissue region. In further or additional embodiments, described herein are compositions comprising at least one plasmonic nanoparticle that comprises a metal, metallic composite, metal oxide, metallic salt, electric conductor, electric superconductor, electric semiconductor, dielectric, quantum dot or composite from a combination thereof. In further or additional embodiments, provided herein is a composition wherein a substantial amount of the plasmonic particles present in the composition comprise geometrically-tuned nanostructures. In certain embodiments, provided herein is a composition wherein plasmonic particles comprise any geometric shape currently known or to be created that absorb light and generate plasmon resonance at a desired wavelength, including nanoplates, solid nanoshells, hollow nanoshells, nanorods, nanorice, nanospheres, nanofibers, nanowires, nanopyramids, nanoprisms, nanostars or a combination thereof. In yet additional embodiments, described herein is a composition wherein the plasmonic particles comprise silver, gold, nickel, copper, titanium, silicon, galadium, palladium, platinum, or chromium.

In some embodiments, provided herein is a composition comprising a cosmetically acceptable carrier that comprises an additive, a colorant, an emulsifier, a fragrance, a humectant, a polymerizable monomer, a stabilizer, a solvent, or a surfactant. In one embodiment, provided herein is a composition wherein the surfactant is selected from the group consisting of: sodium laureth 2-sulfate, sodium dodecyl sulfate, ammonium lauryl sulfate, sodium octech-1/deceth-1 sulfate, lipids, proteins, peptides or derivatives thereof. In one embodiment, provided is a composition wherein a surfactant is present in an amount between about 0.1 and about 10.0% weight-to-weight of the carrier. In yet another embodiment, the solvent is selected from the group consisting of water, propylene glycol, alcohol, hydrocarbon, chloroform, acid, base, acetone, diethyl-ether, dimethyl sulfoxide, dimethylformamide, acetonitrile, tetrahydrofuran, dichloromethane, and ethylacetate. In one embodiment, the composition comprises plasmonic particles that have an optical density of at least about 1 O.D. at one or more peak resonance wavelengths.

In further or additional embodiments, described herein is a composition wherein plasmonic particles comprise a hydrophilic or aliphatic coating, wherein the coating does not substantially adsorb to skin of a mammalian subject, and wherein the coating comprises polyethylene glycol, silica, silica-oxide, polyvinylpyrrolidone, polystyrene, a protein or a peptide. In yet an additional embodiment, the thermomodulation comprises damage, ablation, thermoablation, lysis, denaturation, deactivation, activation, induction of inflammation, activation of heat shock proteins, perturbation of cell-signaling or disruption to the cell microenvironment in the target tissue region. Still further, in certain presentations the target tissue region comprises a sebaceous gland, a component of a sebaceous gland, a sebocyte, a component of a sebocyte, sebum, or hair follicle infundibulum. In further embodiments, the target tissue region comprises a bulge, a bulb, a stem cell, a stem cell niche, a dermal papilla, a cortex, a cuticle, a hair sheath, a medulla, a pylori muscle, a Huxley layer, or a Henle layer.

In another aspect, described herein are methods of performing targeted ablation of tissue. For example, in one embodiment, provided is a method for performing targeted ablation of a tissue to treat a mammalian subject in need thereof, comprising the steps of i) topically administering to a skin surface of the subject the composition of claim 1; ii) providing penetration means to redistribute the plasmonic particles from the skin surface to a component of dermal tissue; and iii) causing irradiation of the skin surface by light. In further or additional embodiments, provided is a method wherein the light source comprises excitation of mercury, xenon, deuterium, or a metal-halide, phosphorescence, incandescence, luminescence, light emitting diode, or sunlight. In still further or additional embodiments, provided is a method wherein the penetration means comprises high frequency ultrasound, low frequency ultrasound, massage, iontophoresis, high pressure air flow, high pressure liquid flow, vacuum, pre-treatment with fractionated photothermolysis or dermabrasion, or a combination thereof. In still further embodiments, provided is a method wherein the irradiation comprises light having a wavelength of light between about 200 nm and about 10,000 nm, a fluence of about 1 to about 100 joules/cm$^2$, a pulse width of about 1 femtosecond to about 1 second, and a repetition frequency of about 1 Hz to about 1 THz.

In a further aspect, provided herein is a composition comprising a cosmetically acceptable carrier, an effective amount of sodium dodecyl sulfate, and a plurality of plasmonic nanoparticles in an amount effective to induce thermal damage in a target tissue region with which the composition is topically contacted, wherein the nanoparticles have an optical density of at least about 1 O.D. at a resonance wavelength of about 810 nanometers or 1064 nanometers, wherein the plasmonic particles comprise a silica coating from about 5 to about 35 nanometers, wherein the acceptable carrier comprises water and propylene glycol.

In yet another aspect, provided is a system for laser ablation of hair or treatment of acne comprising a composition and a source of plasmonic energy suitable for application to the human skin.

DETAILED DESCRIPTION

Figure 1:
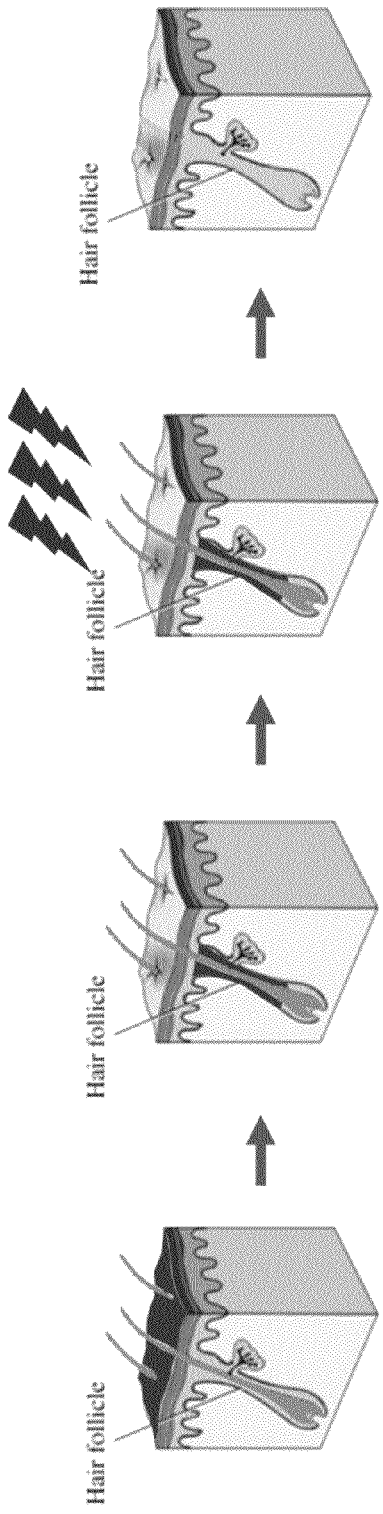
FIG. 1 is illustrative of schematics depicting certain embodiments of the use of formulations for hair removal and acne treatment. Depicted is (A) for hair removal, the plasmonic nanoparticle formulation (black) is 1. applied topically to human skin, 2. delivered deep into the follicle and washed from the skin surface, 3. irradiated with a clinical laser at a wavelength resonant to the peak absorption wavelength of the plasmonic particle, and 4. shed from the follicle along with the damaged hair follicle; and (B) for acne treatment, the plasmonic nanoparticle formulation (black) is 1. applied topically to human skin, 2. delivered specifically into the sebaceous gland and washed from the skin surface, 3. irradiated with a clinical laser at a wavelength resonant to the peak absorption wavelength of the plasmonic particle, and 4. shed from the target site where the accumulated sebum and sebum-producing capabilities of the sebaceous gland are destroyed.
Figure 1:
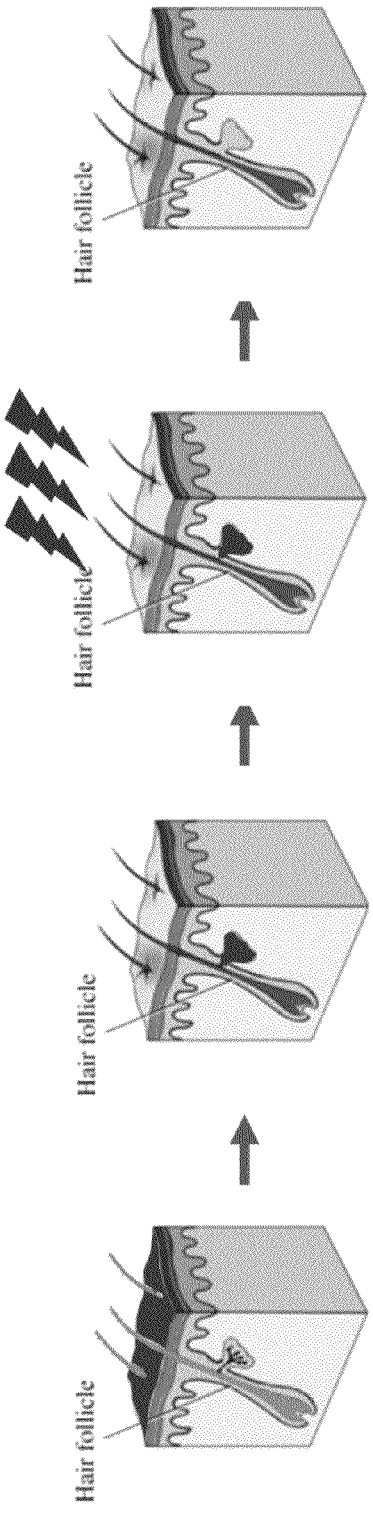

The biology of physiological and pathophysiological tissue growth and remodeling, and alterations in cell morphology is more complex than generally appreciated, involving an interacting network of biological compounds, physical forces, and cell types.

An object of the subject matter described herein is to provide compositions, methods and systems for noninvasive and minimally-invasive treatment of skin and underlying tissues, or other accessible tissue spaces with the use of nanoparticles. The treatment includes, but is not limited to, hair removal, hair growth and regrowth, and skin rejuvenation or resurfacing, acne removal or reduction, wrinkle reduction, pore reduction, ablation of cellulite and other dermal lipid depositions, wart and fungus removal, thinning or removal of scars including hypertrophic scars and keloids, abnormal pigmentation (such as port wine stains), tattoo removal, and skin inconsistencies (e.g. in texture, color, tone, elasticity, hydration). Other therapeutic or preventative methods include but are not limited to treatment of hyperhidrosis, anhidrosis, Frey's Syndrome (gustatory sweating), Homer's Syndrome, and Ross Syndrome, actinici keratosis, keratosis follicularis, dermatitis, vitiligo, pityriasis, psoriasis, lichen planus, eczema, alopecia, psoriasis, malignant or non-malignant skin tumors.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting. Other features of the disclosure are apparent from the following detailed description and the claims.

"Administer" and "administration" as used herein, include providing or causing the provision of a material to a subject, such as by a topical, subdermal, subcutaneous, intradermal, enteral, parenteral, rectal, nasal, intravenous, intramuscularly, intraperitoneal, or other route.

A "carrier suitable for administration" to a subject is any material that is physiologically compatible with a topical or route of administration to a desired vertebrate subject. Carriers can include solid-based, dry materials for formulation; or the carrier can include liquid or gel-based materials for formulations into liquid or gel forms. The specific type of carrier, as well as the final formulation depends, in part, upon the selected route(s) of administration and the type of product.

A "comparable amount" is an amount that is measurably similar to a given reference or standard.

The "components" of a formulation include any products or compounds associated with or contained within it.

An "effective dose", "effective amount" or "therapeutic amount" is an amount sufficient to elicit the desired pharmacological, cosmetic or therapeutic effects, thus resulting in effective prevention or treatment of a disease or disorder, or providing a benefit in a vertebrate subject.

A "therapeutic effect" or "therapeutically desirable effect" refers to a change in a domain or region being treated such that it exhibits signs of being effected in the manner desired, e.g., cancer treatment causes the destruction of tumor cells or halts the growth of tumor cells, acne treatment causes a decrease in the number and/or severity of blemishes, hair removal treatment leads to evident hair loss, or wrinkle reduction treatment causes wrinkles to disappear.

An "isolated" biological component (such as a nucleic acid molecule, protein, or cell) has been substantially separated or purified away from other biological components in which the component was produced, including any other proteins, lipids, carbohydrates, and other components.

A "nanoparticle", as used herein, refers generally to a particle having at least one of its dimensions from about 0.1 nm to about 9000 nm.

A "subject" or "patient" as used herein is any vertebrate species.

As used herein, a "substantially pure" or "substantially isolated" compound is substantially free of one or more other compounds.

A "target tissue" includes a region of an organism to which a physical or chemical force or change is desired. As described herein, exemplary target tissues for acne treatment include a sebaceous gland, while exemplary target tissues for hair removal include a pilosebaceous unit, a hair infundibulum, a hair follicle, or a non-follicular epidermis. A "region" of a target tissue includes one or more components of the tissue. Exemplary target tissue regions include the stem cell niche, bulge, sebaceous gland, dermal papilla, cortex, cuticle, inner root sheath, outer root sheath, medulla, Huxley layer, Henle layer or pylori muscle. A "domain" of a target tissue region includes basement membrane, extracellular matrix, cell-surface proteins, unbound proteins/analytes, glycomatrices, glycoproteins, or lipid bilayer.

A compound that is "substantially free" of some additional contents is largely or wholly without said contents.

A "plasmonic nanoparticle" is a nanometer-sized metallic structure within which localized surface plasmons are excited by light. These surface plasmons are surface electromagnetic waves that propagate in a direction parallel to the metal/dielectric interface (e.g., metal/air or metal/water).

A "light-absorbing nanomaterial" includes a nanomaterial capable of demonstrating a quantum size effect.

As described herein, provided are compositions that contain plasmonic nanoparticles to induce selective thermomodulation in a target tissue.

Plasmonic Nanoparticles.

Such compositions contain from about 2 to about $1 \times 10^{18}$ nanoparticles (e.g., $10^9$ to about $10^{16}$ nanoparticles), such as $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ particles. Preferably, the compositions contain about $10^{11}$ to $10^{13}$ particles so that the amount of particles localized to an effective 1 ml treatment volumes is from $10^9$ to $10^{11}$. Generally, the compositions contain nanoparticles in a concentration of from about 1 O.D. to about 10,000 O.D. For embodiments wherein a greater concentration of nanoparticles to a target region is desired, compositions contain particle concentrations with optical densities of, for example, 10 O.D.-5000 O.D. more specifically 100 O.D.-1000 O.D., or optical densities greater than 1,000 O.D. In certain embodiments wherein increased concentration of nanoparticles to a target region is desired, compositions contain particle concentrations with optical densities (O.D.) of 10 O.D.-1000 O.D., or optical densities greater than 1,000 O.D. In some embodiments these correspond to concentrations of about 1-10% w/w or more of nanoparticles. Determination of O.D. units in a composition is determined using devices and analyses known in the art.

Nanoparticles may be homogenous or heterogeneous in size and other characteristics. The size of the nanoparticle is generally about 0.1 nm to about 50,000 nm (e.g., about 0.1 nm to about 5,000 nm) in at least one dimension. Some variation in the size of a population of nanoparticles is to be expected. For example, the variation might be less than 0.01%, 0.1%, 0.5%, 1%, 5%, 10%, 15%, 25%, 50%, 75%, 100%, 200% or greater than 200%. In certain embodiments where optimal plasmonic resonance is desired, a particle size in the range of from about 10 nm to about 100 nm is provided. Alternatively, in embodiments where enhanced penetration of the nanoparticles into a target tissue region such as a hair follicle is desired, a particle size in the range of from about 100 nm to about 1000 nm is provided. Modulation of particle size present in the composition is also a useful means of concentrating the composition in a target domain. Further, as described herein, nanoparticles having a size range of from about 10 nm to about 100 nm can be used as component of a larger molecular structure, generally in the range of from about 100 nm to about 1000 nm. For example, the plasmonic nanoparticle can be surface coated to increase its size, embedded into an acceptable carrier, or it can be cross-linked or aggregated to other particles, or to other materials, that generate a larger particle. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., hair follicle) and limit delivery to non-target region (e.g. dermis). In one embodiment, the invention comprises a composition comprising at least about 1 O.D. (e.g., at least 10 O.D.) of coated plasmonic nanoparticles (e.g., comprising silica or polyethylene glycol (PEG)) having a mean length in at least one dimension greater than about 30 nanometers, wherein the coated nanoparticles are formulated in an acceptable carrier to be effective in induction of selective thermoablation in a target tissue region with which the composition is contacted, wherein the affinity of the coated nanoparticles for the target tissue region is substantially greater than the affinity of the coated nanoparticles for a non-target tissue region.

Important considerations when generating nanoparticles include: 1) the zeta potential (positive, negative, or neutral) and charge density of the particles and resulting compositions; 2) the hydrophilicity/hydrophobicity of the particles and resulting compositions; 3) the presence of an adsorption layer (e.g., a particle slippage plane); and 4) target cell adhesion properties. Nanoparticle surfaces can be functionalized with thiolated moieties having negative, positive, or neutral charges (e.g. carboxylic acid, amine, hydroxyls) at various ratios. Moreover, anion-mediated surface coating (e.g. acrylate, citrate, and others), surfactant coating (e.g., sodium dodecyl sulfate, sodium laureth 2-sulfate, ammonium lauryl sulfate, sodium octech-1/deceth-1 sulfate, lecithin and other surfactants including cetyl trimethylammonium bromide (CTAB), lipids, peptides), or protein/peptide coatings (e.g. albumin, ovalbumin, egg protein, milk protein, other food, plant, animal, bacteria, yeast, or recombinantly-derived protein) can be employed. Block-copolymers are also useful. Further, one will appreciate the utility of any other compound or material that adheres to the surface of light-absorbing particles to promote or deter specific molecular interactions and improve particle entry into pores or follicles. In some embodiments, the particle surface is unmodified. Modulation of hydrophilicity versus hydrophobicity is performed by modifying nanoparticle surfaces with chemistries known in the art, including silanes, isothiocyanates, short polymers (e.g., PEG), or functionalized hydrocarbons. Polymer chains (e.g., biopolymers such as proteins, polysaccharides, lipids, and hybrids thereof; synthetic polymers such as polyethyleneglycol, PLGA, and others; and biopolymer-synthetic hybrids) of different lengths and packing density are useful to vary the adsorption layer/slippage plane of particles.

Optical Absorption.

Preferred nanoparticles have optical absorption qualities of about 10 nm to about 10,000 nm, e.g., 100-500 nm, 500-750 nm, 600-900 nm, 700-1,000 nm, 800-1,200 nm, or 500-2,000 nm. In specific embodiments, the nanoparticles have optical absorption useful to excitation by standard laser devices or other light sources. For example, nanoparticles absorb at wavelengths of about 755 nm (alexandrite lasers), in the range of about 800-810 nm (diode lasers), or about 1064 nm (Nd:YAG lasers). Similarly, the nanoparticles absorb intense pulsed light (IPL), e.g., at a range of about 500 nm to about 1200 nm.

Assembly.

The nanoparticles provided herein can generally contain a collection of unassembled nanoparticles. By "unassembled" nanoparticles it is meant that nanoparticles in such a collection are not bound to each other through a physical force or chemical bond either directly (particle-particle) or indirectly through some intermediary (e.g. particle-cell-particle, particle-protein-particle, particle-analyte-particle). In other embodiments, the nanoparticle compositions are assembled into ordered arrays. In particular, such ordered arrays can include any three dimensional array. In some embodiments, only a portion of the nanoparticles are assembled, e.g., 5, 10, 15, 20, 25, 30, 35, 40, 45, 50, 55, 60, 65, 70, 75, 80, 86, 90, 95, 99% or greater than 99% of the nanoparticles are assembled in an ordered array. The nanoparticles are assembled by a van der Walls attraction, a London force, a hydrogen bond, a dipole-dipole interaction, or a covalent bond, or a combination thereof.

"Ordered array" "Ordered arrays" can take the form of a macrostructure from individual parts that may be patterned or unpatterned in the form of spheres, colloids, beads, ovals, squares, rectangles, fibers, wires, rods, shells, thin films, or planar surface. In contrast, a "disordered array" lacks substantial macrostructure.

Geometrically Tuned Nanostructures.

The nanoparticles provided herein are formable in all shapes currently known or to be created that absorb light and generate a plasmon resonance at a peak-wavelength or composition of wavelengths from 200 nm to 10,000 nm. In non-limiting examples, the nanoparticles are shaped as spheres, ovals, cylinders, squares, rectangles, rods, stars, tubes, pyramids, stars, prisms, triangles, branches, plates or comprised of a planar surface. In non-limiting examples, the plasmonic particles comprise nanoplates, solid nanoshells, hollow nanoshells nanorods, nanorice, nanospheres, nanofibers, nanowires, nanopyramids, nanoprisms, nanoplates or a combination thereof. Plasmonic particles present in the composition comprise a substantial amount of geometrically-tuned nanostructures defined as 5, 10, 15, 25, 50, 75, 80, 85, 90, 95, 98, 99, 99.9 or greater than 99.9% of particles.

Composition.

The nanoparticle is a metal (e.g., gold, silver), metallic composite (e.g., silver and silica, gold and silica), metal oxide (e.g. iron oxide, titanium oxide), metallic salt (e.g., potassium oxalate, strontium chloride), intermetallic (e.g., titanium aluminide, alnico), electric conductor (e.g., copper, aluminum), electric superconductor (e.g., yttrium barium copper oxide, bismuth strontium calcium copper oxide), electric semiconductor (e.g., silicon, germanium), dielectric (e.g., silica, plastic), or quantum dot (e.g., zinc sulfide, cadmium selenium). In non-limiting examples, the materials are gold, silver, nickel, platinum, titanium, palladium, silicon, galadium. Alternatively, the nanoparticle contains a composite including a metal and a dielectric, a metal and a semiconductor, or a metal, semiconductor and dielectric.

Coating.

Preferentially, the composition contains coated nanoparticles.

| Type of Material | Properties | Exemplary Materials |
|---|---|---|
| biorecognitive material | Moiety with affinity or avidity for a substrate or analyte | Antibody, peptide, phage, DNA, RNA |
| bioactive material | Moiety (e.g., protein, analyte) that interrogates or modulates the activity of biologic entity or cell | Growth factor (e.g. VEGF), cytokine, cell surface receptors, receptor ligands, G-protein, kinase/phosphatase |
| biological material | Material that is sourced from living matter | albumin, ovalbumin, egg protein, milk protein, other food, plant, animal, bacteria, yeast, or recombinantly-derived protein; peptides; enzymes, lipids, fatty acids, sugars |
| biocide material | Material that is active in killing, destroying, or disturbing biological matter | Synthetic or natural pesticides, synthetic or natural anti-microbials |
| dielectric materials | An insulator that may be polarized by an electric field | Silicon, doped semiconductors |
| chemo-recognitive material | Material that is able to interact with a moiety for binding, biological or chemical reactions | Receptor, receptor ligand, chemical molecule |
| chemical active material | Material that causes the transformation of a substance | Aldehyde, halogens, metals |
| Polymer/ dendrimer | Long chain molecule (linear or branched, block or co-block) | PLGA, PEG, PEO, polystyrene, carboxylate styrene, rubbers, nylons, silicones, polysaccharides |
| environmentally sensitive polymer | Surface molecule that changes by its environment (e.g. acid) | Ph sensitive bond, light sensitive bond, heat sensitive bond, enzyme sensitive bond, hydrolytic bond |
| Hydrogel | Polymer with high hydrophilicity and water "ordering" capacity | Synthetic 2-hydroxyethyl metacrylate (HEMA)-based, polyethylene glycol (PEG)-based, PLGA, PEG- |

-continued

| Type of Material | Properties | Exemplary Materials |
|---|---|---|
| | | diacrylate; Natural ionic gels, alginate, gelatin, hyaluronic acids, fibrin |
| Metal | Thin metal coating to achieve improved resonance and/or functionalization capacity | Gold, silver, nickel, platinum, titanium, and palladium. |
| Semi-conductors | Semiconductor layer or core that enhance Plasmon resonance | Silicon and galadium. |
| polymer containing a fluorescent marker | Fluorophore cross linked to a polymer coat or directly to the surface of the particle | Fluorescein, rhodamine, Cy5, Cy5.5, Cy7, Alexa dyes, Bodipy dyes |
| Matrix | Matrix coating that increases solubility of nanoparticles and/or reduces "stickiness" to biological structures | Silica, polyvinyl pyrrolidone, polysulfone, polyacrylamide, polyethylene glycol, polystyrene cellulose, carbopol. |

Biological Molecules.

The composition may contain a peptide, a nucleic acid, a protein, or an antibody. For example a protein, antibody, peptide, or nucleic acid that binds a protein of a follicular stem cell (e.g., keratin 15), a protein, glycomatrix, or lipid on the surface of a cell or stem cell, a protein, peptide, glycomatrix of the extracellular matrix or basement membrane.

Charged Moieties.

The coated nanoparticles may contain charged moieties whereby those charges mediate enhanced or diminished binding to components within or outside the hair follicle via electrostatic or chemical interactions.

Description of Target Tissues.

Topical and Dermatological Applications.

Target tissues for topical and dermatological applications include the surface of the skin, the epidermis and the dermis. Diseases or conditions suitable for treatment with topical and dermatological applications include acne, warts, fungal infections, psoriasis, scar removal, hair removal, hair growth, reduction of hypertrophic scars or keloids, skin inconsistencies (e.g. texture, color, tone, elasticity, hydration), and malignant or non-malignant skin tumors.

As used herein, the term "acne" includes acne vulgaris as well as other forms of acne and related cutaneous conditions, including acne aestivalis, acne conglobata, acne cosmetic, acne fulminans, acne keloidalisnuchae, acne mechanica, acne miliarisnecrotica, acne necrotica, chloracne, drug-induced acne, excoriated acne, halogen acne, lupus miliaris disseminates faciei, pomade acne, tar acne, and tropical acne.

Subdermal Applications.

Target tissues for subdermal applications include the adipose tissue and connective tissue below the integumentary system. Diseases or conditions suitable for treatment with subdermatological applications include wrinkles and tattoos. Other applications include skin rejuvenation and/or resurfacing, the removal or reduction of stretch marks and fat ablation.

Often, a specific region of the target tissue is a hair follicle, a sebaceous gland, a merocrine sweat gland, an apocrine sweat gland, or an arrector pili muscle, within which a specific domain is targeted. For example, the bulge region of the hair follicle is targeted. Because in one embodiment the nanoparticles are useful to thermally ablate hair follicle stem cells for hair removal, regions containing hair follicle stem cells are of particular interest for targeting. Thus, the target tissue region may include a stem cell niche, bulge, sebaceous gland,

| Class of Moiety | Properties | Exemplary Moieties |
|---|---|---|
| Polar moieties | Neutral charge but increases hydrophilicity in water | Hydroxyl groups, isothiocyanates |
| Non-polar moieties | Increases hydrophobicity and or improves solubility | Hydrocarbons, myristoylated compounds, silanes, isothiocyanates |
| Charged moieties | Functional surface modifications that change the zeta potential, isoelectric point, or pKa, and impact adsorption/binding to complementary charge compounds | Amines, carboxylic acids, hydroxyls |
| Ionic moieties | Surface groups that have a single ion | Ammonium salts, chloride salts |
| Basic moieties | Groups that donate a hydrogen ions | Amides, hydroxides, metal oxides, fluoride |
| Acidic moieties | Moieties that accept hydrogen ions | Carboxylic acids, sulfonic acids, mineral acids |
| Oxidative moieties | Moieties that oxidize | Manganese ions, reactive oxygen species |
| Hydrophobic moieties | Moieties that improve solubility in non-aqueous solution and/or improve adsorption on the skin within a hair follicle | Hydrocarbons, myristoylated compounds, silanes |
| Hydrophilic moieties | Moieties that are water-loving and prevent adsorption | PEG, PEO, PLGA |
| Agnostic moieties | Moieties that bind a target cell, structure, or protein of interest | Antibodies, peptides, proteins |
| Antagonistic moieties | Moieties that block the binding to a target of interest | Antibodies, peptides, proteins |
| Reactive moieties | Moieties that react with biological or non-biological components with a resulting change in structure on the target | Aldehydes | dermal papilla, cortex, cuticle, inner root sheath, outer root sheath, medulla, Huxley layer, Henle layer or pylori muscle. Each of these regions may contain cells, stem cells, basement membrane, extracellular matrix, growth factors, analytes, or other biologic components that mediate hair follicle rejuvenation. Disruption or destruction of these components would have a therapeutic effect, e.g. slow or stop the processes that mediate hair regrowth, prevent the secretion of sebum from the sebaceous gland, damage or deter tumor cells, reduce the appearance of wrinkles. Structures can also be targeted that are in close proximity to a desired target for ablation, especially when capable of conducting heat effectively.

Localization Domains.

Provided are compositions containing nanoparticles that preferentially localize to a domain of a target tissue region of a mammalian subject to whom the composition is administered.

Targeting Moieties.

The nanoparticles can be engineered to selectively bind to a domain of the target tissue. For example, the nanoparticles are operably linked to the domain via a biologic moiety, in order to effectively target the nanoparticles to the target tissue domain. Preferably, the moiety contains a component of a stem cell, a progenitor cell, an extracellular matrix component, a basement membrane component, a hair shaft component, a follicular epithelial component, or a non-follicular epidermal component. Biological moieties include proteins such as cell surface receptors, glycoproteins or extracellular matrix proteins, as well as carbohydrates, analytes, or nucleic acids (DNA, RNA) as well as membrane components (lipid bilayer components, microsomes).

Delocalization Domains.

Nanoparticles present in the composition preferentially delocalize away from a domain of a target tissue region. Delocalization domains include specific regions of a tissue into which nanoparticles do not substantially aggregate, or alternatively, are removed from the domain more effectively. In preferred embodiments, the delocalization domain is a non-follicular epidermis, dermis, a component of a hair follicle (e.g., a hair stem cell, a stem cell niche, a bulge, a sebaceous gland, a dermal papilla, a cortex, a cuticle, an inner root sheath, an outer root sheath, a medulla, a Huxley layer, a Henle layer, a pylori muscle), a hair follicle infundibulum, a sebaceous gland, a component of a sebaceous gland, a sebocyte, a component of a sebocyte, or sebum Energy Sources.

Provided herein are nonlinear excitation surface plasmon resonance sources, which include various light sources or optical sources. Exemplary light sources include a laser (ion laser, semiconductor laser, Q-switched laser, free-running laser, or fiber laser), light emitting diode, lamp, the sun, a fluorescent light source or an electroluminescent light source. Typically, the energy source is capable of emitting radiation at a wavelength from about 100, 200, 300, 400, 500, 1000, 2000, 5000 nm to about 10,000 nm or more. The nonlinear excitation surface plasmon resonance source is capable of emitting electromagnetic radiation, ultrasound, thermal energy, electrical energy, magnetic energy, or electrostatic energy. For example, the energy is radiation at an intensity from about 0.00005 mW/cm$^2$ to about 1000 TW/cm$^2$. The optimum intensity is chosen to induce high thermal gradients from plasmonic nanoparticles in regions from about 10 microns to hundreds of microns in the surrounding tissue, but has minimal residual effect on heating tissue in which particles do not reside within a radius of about 100 microns or more from the nanoparticle. In certain embodiments, a differential heat gradient between the target tissue region and other tissue regions (e.g., the skin) is greater than 2-fold, 3-fold, 5-fold, 10-fold, 15-fold, 20-fold, 50-fold, 100-fold, or greater than 100 fold.

The energy can be tuned by monitoring thermal heat gradients on the surface of the skin with a thermal/infrared camera. As demonstrated herein, the methods and systems of the present disclosure provide superior efficacy when a surface plasmon is generated on the nanoparticles by the action of the radiation. Typically, the plasmon is generated in a one-photon mode or, alternatively, a two-photon mode, a multi-photon mode, a step-wise mode, or an up-conversion mode.

Delivery of Radiation.

Physical means of delivery of the energy from the nonlinear excitation surface plasmon resonance source to the target tissue region include a fiber, waveguide, a contact tip or a combination thereof.

Optical sources include a CW optical source or a pulsed optical source, which may be a single wavelength polarized (or, alternatively, unpolarized) optical source capable of emitting radiation at a frequency from about 200 nm to about 10,000 nm. Alternatively, the optical source is a multiple wavelength polarized (or, alternatively, unpolarized) optical source capable of emitting radiation at a wavelength from about 200 nm to about 10,000 nm. The pulsed optical source is generally capable of emitting pulsed radiation at a frequency from about 1 Hz to about 1 THz. The pulsed optical source is capable of a pulse less than a millisecond, microsecond, nanosecond, picoseconds, or femtosecond in duration. For example, a source emitting radiation at a wavelength of 755 nm is operated in pulse mode such that the emitted radiation is pulsed at a duration of 0.25-300 milliseconds (ms) per pulse, with a pulse frequency of 1-10 Hz. In another example, radiation emitted at a wavelength of 810 nm is pulsed at 5-100 ms with a frequency of 1-10 Hz. In a further example, a source emitting radiation at a wavelength of 1064 nm is pulsed at 0.25-300 ms at a frequency of 1-10 Hz. In yet another example, a source emitting intense pulsed light at a wavelength of 530-1200 nm is pulsed at 0.5-300 ms at a frequency of 1-10 Hz. The optical source may be coupled to a skin surface cooling device to reduce heating of particles or structures on the skin surface and focus heating to components within follicles or tissue structures at deeper layers.

Nanoparticle-Containing Compositions.

In order to provide optimal dermal penetration into the target tissue, the plasmonic nanoparticles in certain embodiments are formulated in various compositions. Preferentially, the nanoparticles are formulated in compositions containing 1-10% v/v surfactants (e.g. sodium dodecyl sulfate, sodium laureth 2-sulfate, ammonium lauryl sulfate, sodium octechl/deceth-1 sulfate). Surfactants disrupt and emulsify sebum or other hydrophobic fluids to enable improved targeting of hydrophilic nanoparticles to the hair follicle, infundibulum, sebaceous gland, or other regions of the skin. Surfactants also lower the free energy necessary to deliver hydrophilic nanoparticles into small hydrophobic crevices such as the space between the hair shaft and follicle or into the sebaceous gland. Nanoparticle-containing compositions may also include emulsions at various concentrations (1-20% w/v) in aqueous solutions, silicone/oil solvents, polypropylene gel, propylene glycol or creams (e.g. comprising alcohols, oils, paraffins, colloidal silicas). In other embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Alternatively, a matrix component such as silica, polystyrene or polyethylene glycol is provided in the formulation. Other formulations include components of surfactants, a lipid bilayer, a liposome, or a microsome. A nanoparticle may comprise a larger micron-sized particle.

Effective Doses.

As described herein, an effective dose of the nanoparticle-containing compositions includes an amount of particles required, in some aspects, to generate an effective heat gradient in a target tissue region, such that a portion of the target tissue region is acted upon by thermal energy from excited nanoparticles. A "minimal effective dose" is the smallest number or lowest concentration of nanoparticles in a composition that are effective to achieve the desired biological, physical and/or therapeutic effect(s). Preferentially, the plasmonic nanoparticles have an optical density of 10 O.D.-1,000 O.D. at one or a plurality of peak resonance wavelengths.

Cosmetically Acceptable Carriers.

Provided are cosmetic or pharmaceutical compositions with a plurality of plasmonic nanoparticles and a cosmetically or pharmaceutically acceptable carrier. Generally, the carrier and composition must be suitable for topical administration to the skin of a mammalian subject, such that the plasmonic nanoparticles are present in an effective amount for selective thermomodulation of a component of the skin. Preferentially, the nanoparticles are formulated with a carrier containing 1-10% v/v surfactants (e.g. sodium dodecyl sulfate, sodium laureth 2-sulfate, ammonium lauryl sulfate, sodium octech-1/deceth-1 sulfate) to enable disruption of the epidermal skin barrier, emulsify sebum, improve mixing of hydrophilic nanoparticles with hydrophobic solutions, and reduce entropic barriers to delivering hydrophilic particles to hydrophobic regions of the skin (e.g. between the hair shaft and surrounding sheath or follicle). In some embodiments, the carrier contains a polar or non-polar solvent. For example, suitable solvents include alcohols (e.g., n-Butanol, isopropanol, n-Propanol, Ethanol, Methanol), hydrocarbons (e.g., pentane, cyclopentane, hexane, cyclohexane, benzene, toluene, 1,4-Dioxane), chloroform, Diethyl-ether, water, water with propylene glycol, acids (e.g., acetic acid, formic acid), bases, acetone, isooctanes, dimethyl sulfoxide (DMSO), dimethylformamide (DMF), acetonitrile (MeCN), tetrahydrofuran (THF), dichloromethane (DCM), ethylacetate, tetramethylammonium hydroxide, isopropanol, and others. In other embodiments, a stabilizing agent such as antioxidants, preventing unwanted oxidation of materials, sequestrants, forming chelate complexes and inactivating traces of metal ions that would otherwise act as catalysts, emulsifiers, ionic or non-ionic surfactants, cholesterol or phospholipids, for stabilization of emulsions (e.g. egg yolk lecithin, Sodium stearoyl-lactylate, sodium bis(2-ethylhexyl-sulfosuccinate (AOT)), ultraviolet stabilizers, protecting materials, especially plastics, from harmful effects of ultraviolet radiation is provided. In further embodiments, a composition with a cosmetically acceptable carrier is generated such that the nanoparticles are substantially in a suspension.

Other components are also optionally included, including an emulsion, polymer, hydrogel, matrix, lipid bilayer, liposome, or microsome. Additionally, inclusion of a detectable colorant (e.g., a pigment), a fragrance, a moisturizer, and/or a skin protectant is optional. In some examples, the formulation has a viscosity of above, below or within 0.1-10,000 (e.g., $5e^{-4} \times 10^3$, 1,000), as measured in millipascal-seconds (mPa·s).

Nanoparticle quantities per milliliter in a composition are subject to modification for specific binding and can range from $10^9$ to $10^{18}$ particles but generally about $10^{11}$ to $10^{13}$ nanoparticles per milliliter. Nanoparticle quantities per milliliter in a formulation are subject to modification for specific binding but generally up to about $10^{23}$ nanoparticles per milliliter. In certain embodiments wherein increased concentration of nanoparticles to a target region is desired, compositions contain particle concentrations with optical densities of 10 O.D.-1000 O.D., or optical densities greater than 1,000 O.D. In some embodiments these correspond to concentrations of about 0.1-10% w/w or more of nanoparticles.

Prior to application of nanoparticle formulations, skin and hair follicles can be pre-treated to increase the delivery of nanoparticles to a target region. In some embodiments, hair shafts are cut or removed via shaving, waxing, cyanoacrylate surface peels, calcium thioglycolate treatment, or other techniques to remove the hair shaft and/or hair follicle plugs and create a void wherein nanoparticles can accumulate. Orifices of active or inactive follicles can be blocked by plugs formed of corneocytes and/or other material (e.g. cell debris, soot, hydrocarbons, cosmetics). In some embodiments pre-treatment with surface exfoliation including mechanical exfoliation (e.g., salt glow or microdermabrasion) and chemical exfoliation (e.g., enzymes, alphahydroxy acids, or betahydroxy acids) removes plugs from the orifice of follicles to increase the targeting of nanoparticle formulations to target regions within the hair follicle.

In some embodiments, the nanoparticle formulations are formulated for application by a sponge applicator, cloth applicator, direct contact via a hand or gloved hand, spray, aerosol, vacuum suction, high pressure air flow, or high pressure liquid flow, roller, brush, planar surface, semi-planar surface, wax, ultrasound and other sonic forces, mechanical vibrations, physical manipulation, hair shaft manipulation (including pulling, massaging), physical force, electrophoresis, iontophoresis, thermal manipulation, and other treatments. In some embodiments, nanoparticle formulation treatments are performed alone, in combination, sequentially or repeated 1-24 times. In other embodiments, the plasmonic nanoparticles are capable of selectively localizing to a first component of the skin, where physical massage or pressure, ultrasound, or heat increase the selective localization of the nanoparticles to this first component. Additionally, the nanoparticles are selectively removable from components of the skin other than the first component, such removal accomplished with acetone, alcohol, water, air, peeling of the skin, chemical peeling, waxing, or reduction of the plasmonic compound. Further, in some embodiments the nanoparticles have a coat layer to increase solubility of the nanoparticles in the carrier and/or reduce "stickiness" and accumulation in non-target areas. The subject matter described herein also provides embodiments in which at least a portion of an exterior surface of the nanoparticle is modified, such as to include a layer of a polymer, polar monomer, non-polar monomer, biologic compound, a metal (e.g., metallic thin film, metallic composite, metal oxide, or metallic salt), a dielectric, or a semiconductor. Alternatively, the exterior surface modification is polar, non-polar, charged, ionic, basic, acidic, reactive, hydrophobic, hydrophilic, agonistic, or antagonistic. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., hair follicle) and limit delivery to non-target region (e.g. dermis).

Penetration Means.

Preferably, the compositions of the instant disclosure are topically administered. Provided herein area means to redistribute plasmonic particles from the skin surface to a component of dermal tissue including a hair follicle, a component of a hair follicle, a follicle infundibulum, a sebaceous gland, or a component of a sebaceous gland using high frequency ultrasound, low frequency ultrasound, massage, iontophoresis, high pressure air flow, high pressure liquid flow, vacuum, pre-treatment with Fractionated Photothermolysis laser or derm-abrasion, or a combination thereof. The nanoparticles described herein are formulated to penetrate much deeper—up to several centimeters, or into the panniculus adiposus (hypodermis) layer of subcutaneous tissue. For example, the compositions can be administered by use of a sponge applicator, cloth applicator, spray, aerosol, vacuum suction, high pressure air flow, high pressure liquid flow direct contact by hand ultrasound and other sonic forces, mechanical vibrations, physical manipulation, hair shaft manipulation (including pulling, massaging), physical force, thermal manipulation, or other treatments. Nanoparticle formulation treatments are performed alone, in combination, sequentially or repeated 1-24 times.

Cosmetic and Therapeutic Uses of Plasmonic Nanoparticles.

In general terms, Applicant(s) have created systems and methods for the cosmetic and therapeutic treatment of dermatological conditions, diseases and disorders using nanoparticle-based treatments methods.

Acne Treatment.

Acne is caused by a combination of diet, hormonal imbalance, bacterial infection (*Propionibacterium acnes*), genetic predisposition, and other factors. The nanoparticle-based methods and systems described herein for acne treatment are able to focally target causative regions of the dermis, the sebaceous gland and the hair follicle, and thus have advantages compared to the existing techniques known in the art, including chemical treatment (peroxides, hormones, antibiotics, retinoids, and anti-inflammatory compounds), derm-abrasion, phototherapy (lasers, blue and red light treatment, or photodynamic treatment), or surgical procedures.

In particular, laser-based techniques are becoming an increasingly popular acne treatment, but a substantial limitation is the lack of selective absorptive properties among natural pigments (e.g. fat, sebum) for specific wavelengths of light such that selective heating of one cell, structure, or component of tissue, particularly in the sebaceous glands, infundibulum, and regions of the hair follicle, is not achieved without heating of adjacent off-target tissue. The nanoparticles described herein provide significantly higher photothermal conversion than natural pigments enabling laser energy to be focused to specific cells, structures, or components of tissue within the sebaceous gland, infundibulum, or regions of the hair follicle for selective photothermal damage.

Using the materials and techniques described herein may provide acne treatments of greater duration than existing methodologies. In certain embodiments, tuned selective ablation of the sebaceous gland or infundibulum is achieved as described herein. In particular, plasmonic nanoparticles are specifically localized to regions of hair follicles in or proximate to the sebaceous gland or infundibulum.

Plasmonic nanoparticles exhibit strong absorption at wavelengths emitted by standard laser hair removal devices (e.g., 755 nm, 810 nm, 1064 nm) relative to surrounding epidermal tissue. Thus, irradiation of targeted plasmonic nanoparticles with laser light induces heat radiation from the particles to the adjacent sebum, sebaceous gland, infundibulum, and other acne causing agents.

Hair Removal.

The nanoparticle-based methods and systems described herein for skin treatment have advantages compared to the existing techniques known in the art, including laser-based techniques, chemical techniques, electrolysis, electromagnetic wave techniques, and mechanical techniques (e.g., waxing, tweezers). Such techniques fail to adequately provide permanent hair removal across a breadth of subjects. In particular, subjects having light to medium-pigmented hair are not adequately served by these techniques, which suffer from side-effects including pain and the lack of beneficial cosmetic affects including hair removal. Laser-based techniques are popular in a variety of applications, but a substantial limitation is the lack of selective absorptive properties among natural pigments (e.g. melanin) for specific wavelengths of light such that selective heating of one cell, structure, or component of tissue is achieved without heating of adjacent off-target tissues. The nanoparticles described herein provide significantly higher photothermal conversion than natural pigments enabling laser energy to be focused to specific cells, structures, or components of tissue for selective photothermal damage. The methods described herein are useful for hair removal of all types and pigmentations. For example, melanin, the predominant hair pigment, is an aggregation of chemical moieties including eumelanin and phaeomelanin. Eumelanin colors hair grey, black, yellow, and brown. A small amount of black eumelanin in the absence of other pigments causes grey hair. Types of eumelanin include black eumelanin and brown eumelanin, with black melanin being darker than brown. Generally, black eumelanin predominates in non-European subjects and aged Europeans, while brown eumelanin is in greater abundance in young European subjects. Phaeomelanin predominates in red hair. In another example, vellus hair ("peach fuzz") is a type of short, fine, light-colored, and usually barely noticeable hair that develops on much or most of a subject's body (excluding lips, palms of hand, sole of foot, navel and scar tissue). While the density of vellus hair is generally lower than that of other hair types, there is variation from person to person in the density, thickness, and pigmentation. Vellus hair is usually less than 2 mm long and the follicle containing the vellus hair is generally not connected to a sebaceous gland. Conditions associated with an over-abundance of vellus hair include Cushing's syndrome and anorexia nervosa, such overgrowth being treatable using the methods and compositions described herein. Further, provided are methods of targeting hair growth at a given stage. Hair grows in cycles of various stages or phases. Growth phase is termed "anagen", while "catagen" includes the involuting or regressing phase, and "telogen" encompasses the resting or quiescent phase. Each phase has several morphologically and histologically distinguishable sub-phases. Generally, up to 90% of the hair follicles on a subject are in anagen phase (10-14% are in telogen and 1-2% in catagen). The cycle's length is governed by cytokines and hormones, and varies on different parts of the body. For eyebrows, the cycle is completed in around 4 months, while it takes the scalp 3-4 years to finish. The methods and compositions described herein are sufficient to treat hair of all growth stages or phases.

More permanent reduction or removal of all hair types is provided herein, relative to hair removal treatments known in the art. In certain embodiments, tuned selective ablation of the hair shaft and destruction of stem cells in the bulge region is provided, as described herein. In particular, plasmonic nanoparticles are specifically localized to regions of hair follicles in or proximate to the bulge region, a stem cell-rich domain of the hair follicle. Moreover, the plasmonic nanoparticles are localized in close approximation of ~50-75% of the hair shaft structure.

Plasmonic nanoparticles exhibit strong absorption at wavelengths emitted by standard laser hair removal devices (e.g., 755 nm, 810 nm, 1064 nm) relative to surrounding epidermal tissue. Thus, irradiation of targeted plasmonic nanoparticles with laser light induces heat radiation from the particles to the adjacent stem cells (or in some cases, the architecture of the hair shaft itself), resulting in cell death and a disruption of the normal regenerative pathway.

Non-Malignant and Malignant Skin Tumors.

Laser therapies for the prevention and treatment of non-malignant, malignant, melanoma and non-melanoma skin cancers have been focused largely on photodynamic therapy approaches, whereby photosensitive porphyrins are applied to skin and used to localize laser light, produce reactive oxygen species and destroy cancer cells via toxic radicals. For example, 5-ALA combined with laser treatment has been FDA-approved for the treatment of non-melanoma skin cancer actinic keratoses, and it is used off-label for the treatment of widely disseminated, surgically untreatable, or recurrent basal cell carcinomas (BCC). However, this procedure causes patients to experiences photosensitivity, burning, peeling, scarring, hypo- and hyper-pigmentation and other side effects due to non-specific transdermal uptake of porphyrin molecules. The nanoparticles described herein provide significantly higher photothermal conversion than natural pigments and dyes, enabling laser energy to be focused to specific cells, structures, or components of tissue for selective thermomodulation Using the materials and techniques described herein may provide cancer treatments of greater degree and duration than existing methodologies. In certain embodiments, tuned selective ablation of specific target cells, such as Merkel cells or Langerhans cells, as described herein. In particular, plasmonic nanoparticles are specifically localized to regions of hair follicles where follicular bulge stem cells arise to form nodular basal cell carcinomas and other carcinomas. Plasmonic nanoparticles may also be delivered to other target cells that cause tumors, for example, the interfollicular epithelium, which include the cell of origin for superficial basal cell carcinomas.

Plasmonic nanoparticles exhibit strong absorption at wavelengths emitted by standard laser hair removal devices (e.g., 755 nm, 810 nm, 1064 nm) relative to surrounding epidermal tissue. Thus, irradiation of targeted plasmonic nanoparticles with laser light induces heat radiation from the particles to the adjacent keratinocyte, melanocyte, follicular bulge stem cell, cancer cell, or cancer cell precursor, resulting in cell death or inhibited cell growth for cancer prevention and treatment.

Subdermal Applications.

Target tissues for subdermal applications include the adipose tissue and connective tissue below the integumentary system. Diseases or conditions suitable for treatment with subdermatological applications include wrinkles and tattoos. Other applications include skin rejuvenation and/or resurfacing, the removal or reduction of stretch marks and fat ablation.

Vascular Applications.

Target tissues for vascular applications include arteries, arterioles, capillaries, vascular endothelial cells, vascular smooth muscle cells, veins, and venules. Diseases or conditions suitable for treatment with vascular applications include spider veins, leaky valves, and vascular stenosis. In particular, vein abnormalities account for a substantial proportion of cosmetic diseases or conditions affecting the vasculature. Individuals with vein abnormalities such as spider veins or faulty venous valves suffer from pain, itchiness, or undesirable aesthetics.

Additionally, there are several indication for which ablation of other vessels including arteries, arterioles, or capillaries could provide therapeutic or cosmetic benefit including: 1) ablation of vasculature supplying fat pads and/or fat cells, 2) ablation of vasculature supporting tumors/cancer cells, 3) ablation of vascular birth marks (port-wine stains, hemangiomas, macular stains), and 4) any other indication whereby ablation of vessels mediates the destruction of tissue and apoptosis or necrosis of cells supported by those vessels with therapeutic or cosmetic benefit. Provided herein are methods for using the compositions described herein for the selective destruction of component(s) of veins from plasmonic nanoparticles focally or diffusely distributed in the blood. Plasmonic nanoparticles are combined with a pharmaceutically acceptable carrier as described above and are introduced into the body via intravenous injection. Nanoparticles diffuse into the blood and, in some embodiments, localize to specific vascular tissues. Subsequently, the nanoparticles are activated with laser or light-based systems as known in the art for treating skin conditions such as hair removal or spider vein ablation. Alternatively, image or non-image guided fiber optic waveguide-based laser or light systems may be used to ablate vessel or blood components in larger veins. In one embodiment, a device with dual functions for both injecting nanoparticles and administering light through on optical waveguide may be used. Activated nanoparticles heat blood and adjacent tissue (vessels, vessel walls, endothelial cells, components on or in endothelial cells, components comprising endothelial basement membrane, supporting mesenchymal tissues, cells, or cell components around the vessel, blood cells, blood cell components, other blood components) to ablative temperatures (38-50 degrees C. or higher).

Provided herein is a composition comprising a pharmaceutically acceptable carrier and a plurality of plasmonic nanoparticles in an amount effective to induce thermomodulation of a vascular or intravascular target tissue region with which the composition is intravenously contacted. Furthermore, the composition of plasmonic nanoparticle may comprise a microvascular targeting means selected from the group consisting of anti-microvascular endothelial cell antibodies and ligands for microvascular endothelial cell surface receptors. Also provided is a method for performing thermoablation of a target vascular tissue in a mammalian subject, comprising the steps of contacting a region of the target vascular tissue with a composition comprising a plurality of plasmonic nanoparticles and a pharmaceutically acceptable carrier under conditions such that an effective amount of the plasmonic nanoparticles localize to a domain of the target vascular region; and exposing the target tissue region to energy delivered from a nonlinear excitation surface plasmon resonance source in an amount effective to induce thermoablation of the domain of the target vascular region.

Oral and nasal Applications.

Target tissues for oral applications include the mouth, nose, pharynx, larynx, and trachea. Diseases or conditions suitable for treatment with vascular applications include oral cancer, polyps, throat cancer, nasal cancer, and Mounier-Kuhn syndrome.

Endoscopic Applications.

Target tissues for endoscopic applications include the stomach, small intestine, large intestine, rectum and anus. Diseases or conditions suitable for treatment with vascular applications include gastrointestinal cancer, ulcerative colitis, Crohn's disease, Irritable Bowel Syndrome, Celiac Disease, Short Bowel Sydrome, or an infectious disease such as giardiasis, tropical sprue, tapeworm infection, ascariasis, enteritis, ulcers, Whipple's disease, and megacolon.

Methods of Thermomodulation.

Provided are methods for performing thermomodulation of a target tissue region. A nanoparticle composition comprising a plurality of plasmonic nanoparticles under conditions such that an effective amount of the plasmonic nanoparticles localize to a domain of the target tissue region; and exposing the target tissue region to energy delivered from a nonlinear excitation surface plasmon resonance source in an amount effective to induce thermomodulation of the domain of the target tissue region.

Removal of Non-Specifically Bound Nanoparticles.

Removing nanoparticles localized on the surface of the skin may be performed by contacting the skin with acetone, alcohol, water, air, a debriding agent, or wax. Alternatively, physical debridement may be performed. Alternatively, one can perform a reduction of the plasmonic compound.

Amount of Energy Provided.

Skin is irradiated at a fluence of 1-60 Joules per $cm^2$ with laser wavelengths of about, e.g., 750 nm, 810 nm, 1064 nm, or other wavelengths, particularly in the range of infrared light. Various repetition rates are used from continuous to pulsed, e.g., at 1-10 Hz, 10-100 Hz, 100-1000 Hz. While some energy is reflected, it is an advantage of the subject matter described herein is that a substantial amount of energy is absorbed by particles, with a lesser amount absorbed by skin. Nanoparticles are delivered to the hair follicle, infundibulum, or sebaceous gland at concentration sufficient to absorb, e.g., 1.1-100× more energy than other components of the skin of similar volume. This is achieved in some embodiments by having a concentration of particles in the hair follicle with absorbance at the laser peak of 1.1-100× relative to other skin components of similar volume.

To enable tunable destruction of target skin structures (e.g., sebaceous glands, infundibulum, hair follicles), light-absorbing nanoparticles are utilized in conjunction with a laser or other excitation source of the appropriate wavelength. The laser light may be applied continuously or in pulses with a single or multiple pulses of light. The intensity of heating and distance over which photothermal damage will occur are controlled by the intensity and duration of light exposure. In some embodiments, pulsed lasers are utilized in order to provide localized thermal destruction. In some such embodiments, pulses of varying durations are provided to localize thermal damage regions to within 0.05, 0.1, 0.5, 1, 2, 5, 10, 20, 30, 50, 75, 100, 200, 300, 500, 1000 microns of the particles. Pulses are at least femtoseconds, picoseconds, microseconds, or milliseconds in duration. In some embodiments, the peak temperature realized in tissue from nanoparticle heating is at least 5, 10, 15, 20, 25, 30, 40, 50, 60, 70, 80, 90, 100, 200, 300, or 500 degrees Celsius. In some embodiments that utilize pulsed heating, high peak temperatures are realized locally within the hair shaft without raising the macroscopic tissue temperature more than 0.1, 0.5, 1, 2, 3, 4, 5, 7, 9, 12, 15, or 20 degrees Celsius. In some embodiments short pulses (100 nanoseconds-1000 microseconds) are used to drive very high transient heat gradients in and around the target skin structure (e.g., sebaceous gland and/or hair follicle) from embedded particles to localize damage in close proximity to particle location. In other embodiments, longer pulse lengths (1-10 ms, or 1-500 ms) are used to drive heat gradients further from the target structure to localize thermal energy to stem cells in the bulge region or other components greater than 100 µm away from the localized particles. Fluences of 1-10 Joules per $cm^2$ or 1-30 Joules per $cm^2$ are generally sufficient to thermally ablate follicles that have high particle concentrations and thus higher absorbance than skin (e.g., 1.1-100 times per volume absorbance of skin). These fluences are often lower than what is currently employed (e.g., Diode: 25-40 $J/cm^2$, Alexandrite: 20 J/cm2, Nd:YAG: 30-60 $J/cm^2$) and lead to less damage to non-follicular regions, and potentially less pain.

Plasmon Resonance Systems.

Provided are plasmon resonance systems containing a surface that includes a plurality of plasmonic nanoparticles, and a nonlinear excitation source. Optionally, the system contains a means to generate thermal heating of the surface. Preferably, the surface is a component of skin that is targeted for cosmetic or therapeutic treatment (e.g., bulge region for hair removal, infundibulum or sebaceous gland for acne prevention). Also provided as a component of the system is a means for delivering plasmonic nanoparticles to the skin surface, such as an applicator, a spray, an aerosol, vacuum suction, high pressure air flow, or high pressure liquid flow. Further provided are means of localizing plasmonic nanoparticles to a component of the skin (e.g., hair follicle, bulge region, sebaceous gland, infundibulum). Useful surface delivery means include a device that generates high frequency ultrasound, low frequency ultrasound, heat, massage, contact pressure, or a combination thereof.

Further provided are systems that contain a removal means for removing nanoparticles on a non-follicular portion of the skin. The removal means includes at least one of acetone, alcohol, water, air, chemical peeling, wax, or a compound that reduces the plasmonic compound.

In addition, the systems of the present disclosure provide nonlinear excitation source that generates a continuous wave optical source or a pulsed optical source. Alternatively, the nonlinear excitation source is capable of generating electromagnetic radiation, ultrasound, thermal energy, electrical energy, magnetic energy, or electrostatic energy. Provided are systems wherein the nonlinear excitation source is capable of irradiating the nanoparticles with an intensity from about 0.00005 $mW/cm^2$ to about 1000 $TW/cm^2$. Further, the nonlinear excitation source is capable of functioning in a one-photon mode, two-photon mode, multi-photon mode, stepwise mode, or up-conversion mode. A fiber, a waveguide, a contact tip, or a combination thereof may be used in the instant systems.

In some embodiments, the system contains a monitoring device such as a temperature sensor or a thermal energy detector. In other embodiments, the systems also contain a controller means for modulating the nonlinear excitation source (e.g., a "feedback loop controller"). In a related embodiment, the system contains a means for detecting a temperature of the surface or a target tissue adjacent to the surface, wherein the controller means modulates the intensity of the nonlinear excitation source and/or the duration of the excitation. In such embodiments, the controller means preferably modulates the intensity of the nonlinear excitation source such that a first component of the hair follicle is selectively thermoablated relative to a second component of the hair follicle. In further embodiments, a cooling device is directly contacted with the skin during irradiation to minimize the heating of nanoparticles or skin at the surface, while nanoparticles that have penetrate more deeply into the follicle, skin, or sebaceous gland heat to temperatures that selectively ablate the adjacent tissues.

Skin is an exemplary target tissue. The skin preferably contains a hair follicle and/or a sebaceous gland, where the nonlinear excitation source generates energy that results in heating the skin in an amount effective to induce thermomodulation of a hair follicle, a infundibulum, a sebaceous gland, or a component thereof, such as by heating sufficient to cause the temperature of the skin to exceed 37° C., such as 38° C., 39° C., 40° C., 41° C., 42° C., 43° C., 44° C., 45° C., 46° C., 47° C., 48° C., 49° C., to about 50° C. or greater.

Methods of Formulation.

Also provided are methods for formulating the nanoparticles of the present disclosure into a form suitable for use as described herein. In particular, the nanoparticle compositions are generated by:
a) forming a first mixture containing a plurality of nanoparticles and a first solvent;
b) exchanging the first solvent for a second solvent to form a second mixture; and
c) combining the second mixture and a cosmetically or pharmaceutically acceptable carrier; thereby forming a nanoparticle composition.

The exchanging step is optionally performed using liquid chromatography, a solvent exchange system, a centrifuge, precipitation, or dialysis. Preferably, the nanoparticles are surface modified through a controlled reduction step or an oxidation step. Such surface modification may involve a coating step, such as the adsorbance of a monomer, polymer, or biological entity to a surface of the nanoparticle. Typically, the coating step involves contacting the nanoparticles with an oxidative environment. Further, the coating step may include monomer polymerization to create polymer coat.

The methods described herein may also include the steps of dissolving the nanoparticles in a non-polar solvent and subsequently mixing the dissolved nanoparticles with a polar solvent so as to encapsulate the nanoparticles in an emulsion. Further, the addition of surfactants (e.g. sodium dodecyl sulfate, sodium laureth 2-sulfate, ammonium lauryl sulfate, sodium octech-1/deceth-1 sulfate) at concentrations of 0.1-10% may be used to disrupt the epidermal skin barrier, emulsify the sebum and enable improved mixing of hydrophilic nanoparticles in aqueous solutions. Further, a concentration of the nanoparticles such as centrifugation or lyophilization may be employed. Further, the nanoparticles may be pre-treated with heat or radiation. Also provided is the optional step of conjugating a biological entity or plurality of biological entities to the nanoparticles. Such a conjugating step may involve a thiol, amine, or carboxyl linkage of the biological entities to the nanoparticles.

Diseases and Disorders.

The present disclosure can be used on human (or other animal) skin for the treatment of wrinkles and other changes related to photo-aging or chronologic aging (generally termed skin rejuvenation), for the treatment of diseases including skin diseases, for the reduction of acne and related disorders such as rosacea, folliculitis, pseudofolliculitis barbae or proliferative or papulosquamous disorders such as psoriasis, for the stimulation or reduction of hair growth, and for reduction of cellulite, warts, hypopigmentation such as port-wine stain (PWS; nevus flammeus), birthmarks, hyperhidrosis, varicose veins, pigment problems, tattoos, vitiligo, melasma, scars, stretch marks, fungal infections, bacterial infections, dermatological inflammatory disorders, musculoskeletal problems (for example, tendonitis or arthritis), to improve healing of surgical wounds, burn therapy to improve healing and/or reduce and minimize scarring, improving circulation within the skin, and the like.

The present disclosure can also be useful in improving wound healing, including but not limited to chronic skin ulcers, diabetic ulcers, thermal burn injuries, viral ulcers or disorders, periodontal disease and other dental disease. The present disclosure can be useful in treating the pancreas in diabetes. The present disclosure can be useful for in vitro fertilization enhancement, and the like. The present disclosure, in certain embodiments, is also useful in enhancing the effects of devices that create an injury or wound in the process of performing cosmetic surgery including non-ablative thermal wounding techniques for treating skin wrinkles, scars, stretch marks and other skin disorders. Under such circumstances, it may be preferable to use conventional non-ablative thermal treatments in combination with the methods of the present disclosure. The instant application, in certain embodiments, are used in conjunction with micro- or surface abrasion, dermabrasion, or enzymatic or chemical peeling of the skin or topical cosmeceutical applications, with or without nanoparticle application to enhance treatment, as the removal of the stratum corneum (and possibly additional epithelial layers) can prove beneficial for some treatment regimen. The methods of the present disclosure are particularly applicable to, but are not limited to, acne treatment, hair removal, hair growth/hair follicle stimulation, reduction/prevention of malignant and non-malignant skin tumors, and skin rejuvenation, as described herein.

The dermatologically therapeutic methods described herein may be formed using nanoparticle irradiation alone, nanoparticle irradiation in combination with nano- or microparticles, or nanoparticle irradiation with a composition comprising nano- or microparticles and one or more therapeutic agents. Such nanoparticle irradiation may be produced by any known nanoparticle generator, and is preferably a focused nanoparticle generator capable of generating and irradiating focused nanoparticle waves. Additionally, nanoparticle waves can be focused in tissues to provide damage to local areas with a desirable size and shape.

EXAMPLES

Example 1

Generation of Plasmonic Nanoparticles for Thermomodulation

Plasmonic nanoparticles, including nanorods, hollow nanoshells, silicon nanoshells, nanoplates, nanorice, nanowires, nanopyramids, nanoprisms, nanoplates and other configurations described herein and known to those skilled in the art, are generated in size ranges from 1-1000 nm under conditions such that surface properties that facilitate deep follicular penetration. Surface properties can be varied on one or multiple (2, 3, or 4) different dimensions to increase nanoparticle concentration in a target tissue domain. Penetration into follicular openings of 10-200 um can be maximized using the nanoparticles described herein. Here, nanoparticles sized in the range of about 10 to about 100 nm are generated, and are preferably assembled or formulated into multiparticular structures having a size in the range of 100-300 nm. Alternatively, a coating (e.g., silica) is grown on unparticular structures to increase the particle size to the range of 100-300 nm or more.

Surface-Modified Plasmonic Nanoparticles.

An exemplary preparation of surface-modified plasmonic nanoparticles is provided as follows. Plasmonic nanoparticles are synthesized with stable cetryltrimethylamonium bromide (CTAB) coating and concentrated from an optical density of 1 O.D. to 100, 200, 300, 400, or 500 O.D. through one to three cycles of centrifugation at 16,000 rcf, with supernatant decanting. Alternatively, CTAB-coated nanoparticles are concentrated and resuspended in 250 Amol/L 5-kDa methylpolyethylene glycol (PEG)-thiol to make PEG-coated nanoparticles. Verification that PEG polymer stocks are fully reduced is performed using spectrophotometry to measure the thiol activity of polymer-thiols with 5,5-dithiobis(2-nitrobenzoic acid) against a DTT gradient. The solution of methy-PEG-thiol and CTAB-coated nanoparticles is mixed at room temperature for 1 h then dialyzed against 5 kDa MWCO in 4 L distilled water for 24 h. Dialyzed samples are processed through 100-kDa filters to remove excess polymer. Quantification of the number of PEG polymers per particle is performed by surface-modifying nanoparticles with amino-PEG-thiol polymer and quantifying the number of amines with an SPDP assay. For test formulations, 100 O.D. solutions of CTAB-coated plasmonic nanoparticles are made in distilled water, and 100 O.D. PEG-coated plasmonic nanoparticles are made in distilled water, ethanol, DMSO, or mineral oil. Plasmonic nanoparticles with silica shells are created by reacting nanoparticles with silicates such as tetra-ethyl-orthosilicate (TEOS), sodium silicate, aminopropyletriethoxysilane (APTS), etc. to thicknesses of 5-50 nm or more. Control, vehicle-only formulations contain no nanoparticles.

Embedded Nanoparticles.

Nanoparticles are embedded (or encapsulated) in materials, which allows for the generation of a diverse range of sizes to tune their size. Particle sizes in the range of 100-2000 nm or 200-2000 nm have been shown to enter the hair follicle without penetrating the dermis. Nanoparticles are encapsulated in silica, a synthetic polylactide/co-glycolide co-polymer, porous lauryllactame/caprolactam nylon co-polymer, hydroxyethylcellulose, polyelectrolyte monolayers, or alternatively, in natural hydrogels such as hyaluronic acid, without significantly altering plasmon resonance properties. Nanoparticles are embedded within 100-2000 nm materials or 200-2000 nm materials without covalent attachment or by cross-linking of amines, carboxyls or other moieties on the nanoparticle surface to the polymer structure. The surface of the 100-2000 nm material or 200-2000 nm material may be modified for an optimal zeta potential, hydrophilicity/hydrophobicity, and/or adsorption layer through techniques described herein. Furthermore, the shape of the aspect ratio of the polymer can be modified from low to high to increase concentrations and depths of penetration of the embedded plasmonic nanoparticles. The nanoparticles advantageously have an aspect ratio greater than about 1.

Example 2

Formulation of Thermoablative Plasmonic Nanoparticles for Topical Delivery

Nanoparticles are generated as in Example 1 using an appropriate solvent (e.g., water, ethanol, dimethyl sulfoxide). The mixture comprising a plurality of nanoparticles in water is concentrated to about 100-500 O.D. and exchanged for a new solvent by liquid chromatography, a solvent exchange system, a centrifuge, precipitation, or dialysis. The solvent may include an alcohol (e.g., n-Butanol, isopropanol, n-Propanol, Ethanol, Methanol), a hydrocarbon (e.g., pentane, cyclopentane, hexane, cyclohexane, benzene, toluene, 1,4-Dioxane), chloroform, Diethyl-ether, water, an acid (e.g., acetic acid, formic acid), a base, acetone, dimethyl sulfoxide (DMSO), dimethylformamide (DMF), acetonitrile (MeCN), tetrahydrofuran (THF), dichloromethane (DCM) or ethylacetate. The new solvent is combined with a cosmetically or pharmaceutically acceptable carrier, thereby forming a nanoparticle composition. Generally, the particles and carrier will form an emulsion.

Plasmonic nanoparticle formulations are provided that amplify or expedite the penetration of nanoparticles into hair follicles. In some embodiments, nano- and micro-emulsions facilitate partitioning within lipid-rich skin compartments such as the hair follicle. In some embodiments, nanoparticles are formulated in compositions containing 0.5-2% v/v surfactants to enable disruption of the epidermal skin barrier, emulsification of sebum, and improved mixing of hydrophilic nanoparticles in hydrophobic solutions or targeting to hydrophobic space in the skin (e.g. between the hair shaft and surrounding follicle). Formulations of nanoparticles are also provided at various concentrations (1-20% w/v) in aqueous solutions, silicone/oil solvents, polypropylene gel, propylene glycol or creams (e.g. containing alcohols, oils, paraffins, colloidal silicas). In some embodiments, light-absorbing nanoparticles are utilized in solutions having tailored pH, temperature, osmolyte concentration, viscosity, volatility, and other characteristics to improve light-absorbing nanoparticle entry into hair follicles.

Formulations are prepared to maximize nanoparticle stability (degree of aggregation in solution), nanoparticle concentration, and nanoparticle absorbance (degree of laser-induced heating at different concentrations).

Figure 2:
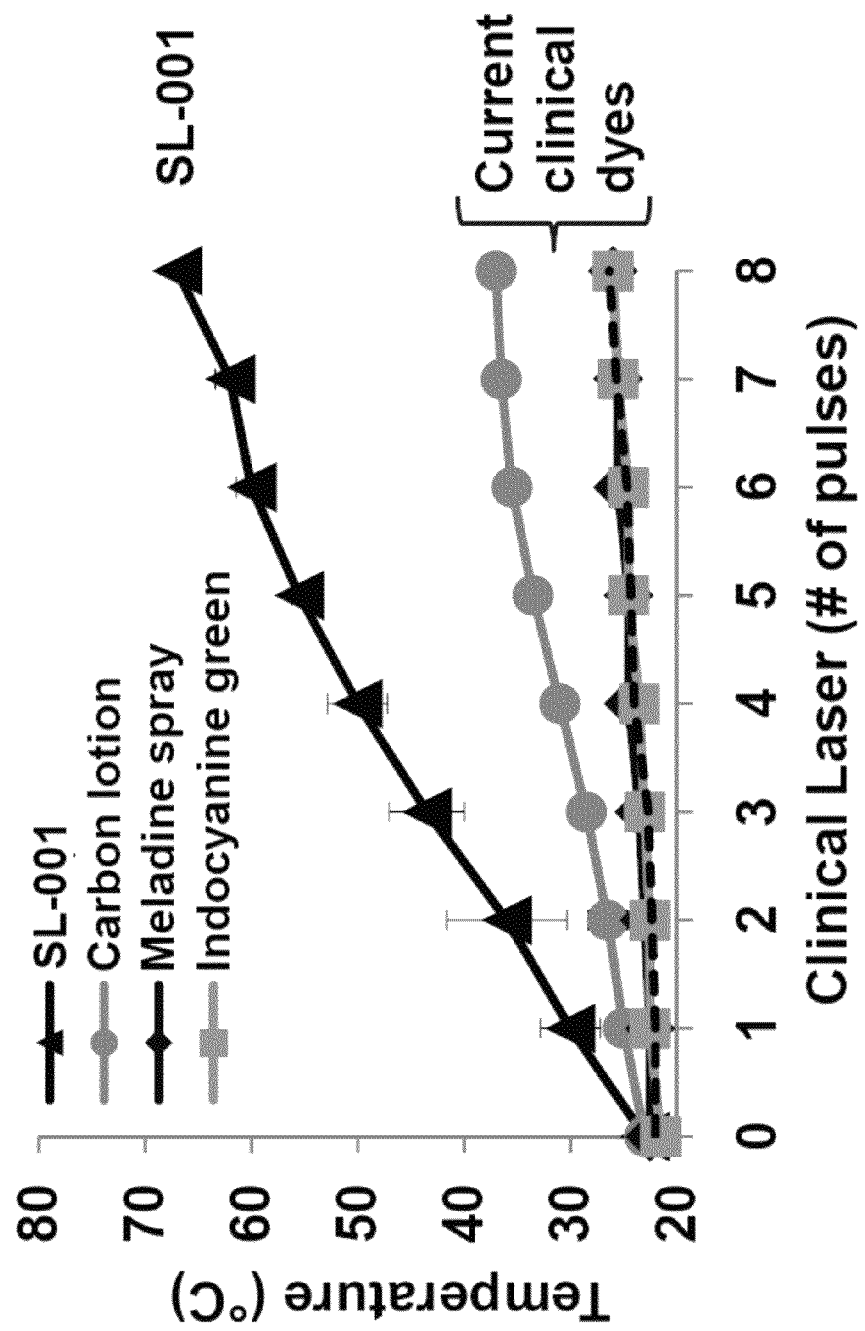
FIG. 2 is illustrative of a temperature profile of certain embodiments of the formulations of plasmonic nanoparticles (SL-001, triangles) provided herein compared to exemplary current clinical dyes carbon lotion (circles), meladine spray (diamonds), and indocyanine green (squares), after exposure to 1064 nm, 20 J/cm$^2$, 55 ms laser pulses. SL-001 and dyes were equally diluted at 1:1000 from clinical concentration (SL-001 1000 O.D., carbon 20-200 mg/ml, meladine 1 mg/ml, ICG 5 mg/ml). n=3, error S.D. of mean.

When formulations of plasmonic nanoparticles are illuminated with a clinical laser with a wavelength coincident to the peak absorption wavelength of the particle, the formulation heats to thermoablative temperatures more rapidly and to a greater degree than conventional clinical absorptive dyes. FIG. 2 compares the temperature profile of plasmonic particles (1020 nm peak absorption wavelength) to conventional clinical dyes carbon lotion, meladine spray and indocyanine green after exposure to 1064 nm, 20 J/cm$^2$, 55 ms laser pulses. The temperature increase caused by pulsed 1064 nm laser light was more than 2.5 times greater for the plasmonic solution, compared to conventional clinical dyes used at the same dilution (1:1000 dilution from clinical concentration, where clinical concentrations are as follows: carbon 20-200 mg/ml, meladine 1 mg/ml, indocyanine green 5 mg/ml).

Example 3

Use of Plasmonic Nanoparticles for Thermomodulation of Hair

Individuals having blonde, red, gray, or lightly-colored hair are not adequately treated with existing light-based hair removal techniques. Provided herein are methods for using the compositions described herein for the selective removal or reduction of untreated blonde, red, gray, or lightly-colored hair. Plasmonic nanoparticles generated and formulated as described above are introduced into a target tissue region, generally a skin region, and activated with laser-based hair removal systems as known in the art in order to achieve effective hair removal.

To achieve maximal penetration depth and concentration of plasmonic nanoparticles in the hair follicle and/or near components of the sebaceous gland including the sebaceous duct, the sebum, the epithelial linking of the sebaceous gland, and/or near the bulge region including the stem cells, stem cell niche, epithelial lining of the bulge region, and/or near the follicular bulb, an optimal particle size of 30-800 nm (e.g., 100-800 nm) containing one or several plasmonic nanoparticles is constructed. Nanoparticles encapsulating plasmonic nanoparticles can be formulated from any number of polymers or matrices. In some embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Preferentially, a matrix component such as silica, polystyrene or polyethylene glycol is provided in the formulation to improve particle stability and enable facile removal from the skin surface after application and follicle targeting. Other formulations include component of surfactants (e.g. sodium dodecyl sulfate, sodium laureth 2-sulfate, ammonium lauryl sulfate, sodium octech-1/deceth-1 sulfate), a lipid bilayer, a liposome, or a microsome. Plasmonic nanoparticles including nanorods, nanoshells, nanospheres, nanoplates, or nanorice can be encapsulated within a the polymer or lipid-based nanoparticle or matrix or deposited on the particle surface. Alternatively, nanoparticles in the size range of 100-250 nm, 250-500 nm, 800 nm-1500 nm, or greater than 1500 nm can be used.

Pre-treatment of skin with mechanical or chemical exfoliation is used in some embodiments to remove hair-plugs and "open" the follicle for particle delivery. Additionally, hairs can be shaven or waxed to create a void in the hair follicle for particles to fill. The use of physical or thermal force amplifies or expedites the penetration of light absorbing nanoparticles and conjugates thereof into hair follicles, in part by causing dilation of the hair follicle prior to application of the nanoparticles. For example, ultrasound and other sonic forces, mechanical vibrations, hair shaft manipulation (including pulling), physical force, thermal manipulation, and other treatments are utilized to improve entry of light-absorbing nanoparticles into hair follicles. Nanoparticle formulation treatments are performed alone, in combination, sequentially or repeated 1-24 times.

An applicator is used to uniformly apply the composition of nanoparticles into follicles. The applicator can be a sponge, a cloth, direct contact from a finger, a tube, a syringe, a device that applies suction, an aerosol, a spray, or other means known in the art. In one example, a formulation of 1 ml of plasmonic nanoparticles at a concentration of 100 O O.D. with peak resonance of 810 nm is applied to approximately 200 $cm^2$ area of the skin of an adult human subject with a syringe. A cloth is used to evenly distribute solution across the skin area and into the hair follicles. Deep massage from a mechanical vibrator for 2 minutes with or without 1 MHz ultrasound for 5 minutes, is applied to drive particles deep into the follicle. Particles penetrate 50-75% down the full length of the hair shaft at concentrations sufficient to heat skin in a 100 μm radius at incremental temperatures of 5-20-fold greater than is generated in similar volumes of adjacent skin when irradiated by a Diode (810 nm) laser. Acetone, ethanol, or a debriding agent can be used to remove all particles from the surface of the skin that have not deposited in the follicle, in order to reduced or prevent non-follicular heating of the skin.

Nanoparticle formulations are tested in ex vivo animal samples, ex vivo human skin samples, and in vivo human skin including the assessment of: 1) depth of nanoparticle penetration into hair follicles; 2) particle concentration achieved; 3) degree of heating achieved at delivered nanoparticle concentrations; and 4) efficacy of photothermal destruction including temporary and permanent hair removal, 5) clearance of nanoparticles after treatment. To assess nanoparticle penetration depths, plasmonic nanoparticles surface-functionalized with fluorescent molecules are visualized by fluorescence microscopy after histological sectioning or follicular biopsy (removal of hair shaft). Alternatively, plasmonic nanoparticles are directly visualized by dark field microscopy after histological sectioning or follicular biopsy. To assess nanoparticle concentrations at various depths along the follicle, excised skin samples are separated by tape stripping or heat-based techniques, samples are dissolved for bulk analysis of metal concentration by ICP-MS (inductively coupled plasma-mass spectrometry). The macroscopic degree of heating is validated by infrared thermography of skin samples, and by assessment of skin sections subject to laser exposure for thermal damage markers. Finally, one can measure efficacy of photothermal destruction at the nanoparticle accumulation site by analyzing histological cellular lesions at the target site, including the follicular hair shaft, inner root sheath, outer room sheath, and bulge region containing the stem cell niche, which contains the stem cells that contribute to new hair growth. As the bulge region is generally localized about midway (~50% down the length of) the hair shaft, permanent hair removal is sufficiently achieved by accumulation of plasmonic nanoparticles to this depth. In some situations, nanoparticle delivery may also generate a heat gradient emitting further down the hair shaft. Animal studies are useful to demonstrate the efficacy of unpigmented hair removal by comparing heat profiles, thermal ablation of hair shaft, and thermal damage of bulge stem cells in treated hairless rodents, albino rodents and dark-haired rodents. Efficacy on live human skin is measured by measuring hair counts at 3 and 12 month follow ups. Biopsies are taken from select patients at 2, 4, and 6 week follow ups to verify that nanoparticles are cleared from the skin without embedding in the dermis.

Hair Follicle Penetration of Fluorescently-Labeled Nanoparticles Determined Using Porcine Skin Explants and Confocal Imaging.

Figure 3:
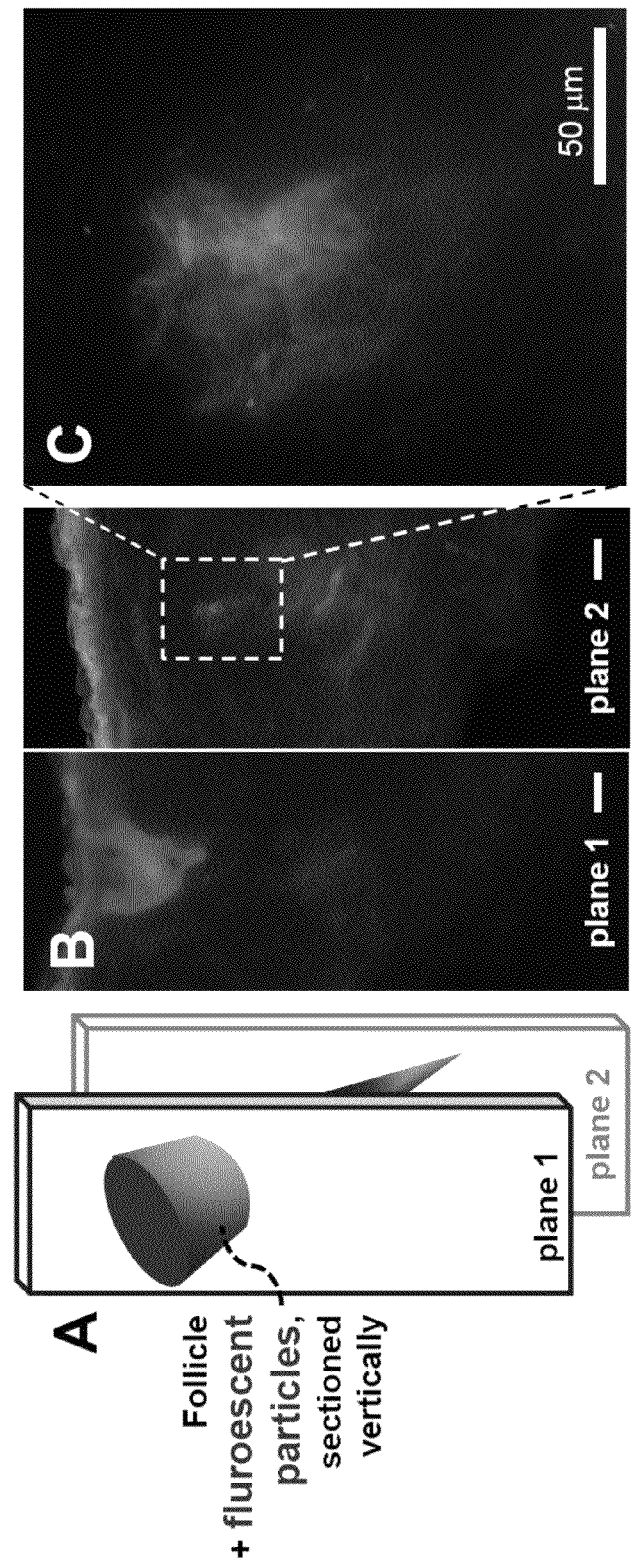
FIG. 3 is illustrative of hair follicle penetration of fluorescently-labeled nanoparticles determined using porcine skin explants and confocal imaging of certain embodiments of the subject matter described herein. Depicted is (A) schematic of treated porcine skin, sectioned and imaged at an angle to the follicle, in two serial 60 μm planes: 'plane 1' (showing follicle infundibulum) and 'plane 2' (showing deep follicle); (B) representative confocal images show red fluorescent nanoparticles (548 nm) within superficial and deep follicle, but not in underlying dermis; and (C) red fluorescent nanoparticles retained in the deep follicle (~400 μm) at high magnification. Green is tissue autofluorescence.

A 25 mg/ml aqueous solution silicon dioxide-coated nanoparticles (200 nm diameter) was contacted with freshly thawed porcine skin, after which excess nanoparticle suspension was removed and manual massage was performed for three minutes. The explant was sectioned and subjected to confocal imaging. As shown in FIG. 3A, explant sections were imaged at angles to the hair follicles in 60 μm planes; Plane 1 shows the follicle infundibulum, while Plane 2 shows the distal regions of the follicle. FIG. 3B demonstrates representative confocal images showing that red nanoparticles (548 nm absorbance) are visible within both the superficial and deep follicles, but are not detectable in dermal layers beneath the follicles. FIG. 3C shows high-magnification imaging of red nanoparticles localized to and retained within a deep follicle (~400 μm). Green color indicates tissue autofluorescence (488 nm).

Hair Follicle Penetration of Plasmonic Nanoparticles Determined Using Porcine Skin and Dark Field Imaging.

Figure 4:
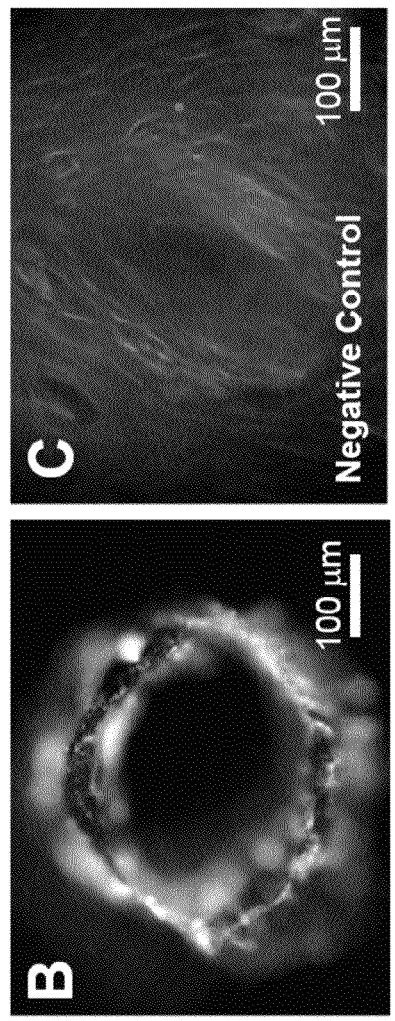
FIG. 4 is illustrative of a hair follicle penetration of plasmonic nanoparticles determined using porcine skin explants and dark field imaging. Shown is (A) schematic of treated porcine skin, sectioned and imaged horizontal to the follicle; (B) bright blue plasmonic particles are visible in a 1.2 mm deep section, and are differentiated from (C) untreated (negative control) porcine skin, where no pigments are visible.

A 100 O.D. suspension of plasmonic nanoparticles (200 nm diameter) was contacted with freshly thawed porcine skin, after which excess nanoparticle suspension was removed and manual massage performed for three minutes. The procedure was repeated for a total of 3 applications, and surface residue removed with several 3-5 applications of alternating water and ethanol. The skin sample was excised, fixed, sectioned along horizontal plane and subjected to dark field imaging. As shown in FIG. 4A, skin samples were sectioned and imaged horizontal to the hair follicle at various depths. In skin section images, plasmonic nanoparticles were observed as bright blue color point sources at depths up to 1.2 mm deep in porcine follicle spaces (FIG. 4B). Control samples with no plasmonic nanoparticles were clearly differentiated (FIG. 4C). ICP-MS is also performed on skin sections to assess nanoparticle concentrations at various depths along the follicle.

Hair Follicle Penetration of Nanoparticles in Hairless Rodents, Albino Rodents and Dark-Haired Rodents.

White-haired Swiss Webster mice (n=3) at 8 weeks old are anesthetized with injectable ketamine/xylazine anesthetic solution and dorsal back skin and hair washed and dried. Prior to formulation administration, three 10 cm×10 cm areas are demarcated by permanent marker on each mouse and subjected to hair removal by 1) electric razor, 2) Nair depilation reagent, or 3) warm wax/rosin mixture application and stripping. Each mouse is treated by pipette with up to 3 nanoparticle formulations, in quadruplicate 5-µl spot sizes per demarcated skin area (up to 12 spots per area or 36 spots per mouse). Precise spot locations are demarcated with pen prior to pipetting. Duplicate treatment spots on the dorsal left side are massaged into skin for 5 minutes, while duplicate treatment spots on the dorsal right side are applied without massage. Thirty minutes after application, mice are sacrificed by carbon dioxide asphyxiation and cervical dislocation, and skin is carefully excised and punched into sections along spot size demarcations. Skin biopsies are fixed in 10% paraformaldehyde, paraffin-embedded, and cut into 5-um sections on a microtome in transverse directions. Slides with mounted paraffin sections are deparaffinized and stained with hematoxylin and eosin (H&E) or kept unstained for dark field microscopy. Using H&E staining, light microscopy and/or dark field microscopy, greater than 50 follicles per formulation are imaged, and scoring is performed for skin sections for visible macroscopic nanoparticle accumulation in the follicle, along the hair shaft, at the site of the putative bulge stem cell niche, and at the depth of the follicle bulb. On serial histological sections, a silver enhancement staining kit based on sodium thiosulfate may be used to enlarge the plasmonic nanoparticle signal via the precipitation of metallic silver. Phase and dark field micrographs are captured and used to record the depths of follicular penetration for each nanoparticle formulation and method of application. ICP-MS is also performed on skin sections to assess nanoparticle concentrations at various depths along the follicle.

Assessment of Photothermal Destruction at the Nanoparticle Accumulation Site.

Treated areas of pig, human or mouse skin are irradiated with a laser coincident with the peak absorption wavelength of nanoparticles (e.g. 1064 nm YAG laser for 1020 nm plasmonic particles) using clinical parameters (1 s exposure of 30-50 $J/cm^2$ and a pulse width of 10-50 ms). To determine microscopic photothermal damage of target skin structures such as the hair follicle and hair follicle bulge stem cells, at ten days after application and irradiation, human subjects receive lidocaine injections to numb treatment areas and skin is carefully excised and punched into sections along spot size demarcations. Fresh human skin biopsies or explanted human and animal skin samples are fixed in 10% paraformaldehyde, paraffin-embedded, and cut into 5-um sections on a microtome in transverse directions, or they are fixed in Zamboni's solution with 2% picric acid and cryosectioned by freezing sliding microtome. Slides with mounted paraffin sections are deparaffinized and stained with hematoxylin and eosin (H&E). Histological sections are examined at various depths for markers of thermal damage and inflammation. Hematoxylin and eosin (H&E) is used to image skin and follicle microanatomy and indicate degeneration of hair shafts, atrophy of sebaceous glands, and cell vacuolization (indicating cellular damage). Nitro blue tetrazolium chloride (NBTC), a lactate dehydrogenase stain that is lost upon thermal injury to cells, is used to assess damage to keratinocytes. Cellular damage in follicles of skin samples receiving plasmonic nanoparticle plus laser treatment is scored and compared to those receiving laser treatment alone. Live treated human skin areas are also followed clinically for 2 weeks to 3 months following plasmonic nanoparticle+laser treatment, or during repeated plasmonic nanoparticle+laser treatments, and compared to baseline digital photograph taken prior to first treatment, and to negative control laser only treatments. Clinical observations of hair removal, as well as erythema, edema, discomfort, irritation or scarring, are noted to determine degree of non-specific thermal damage.

Effect of Plasmonic Particle Coating on Specificity of Delivery and Photothermal Heating.

Figure 5:
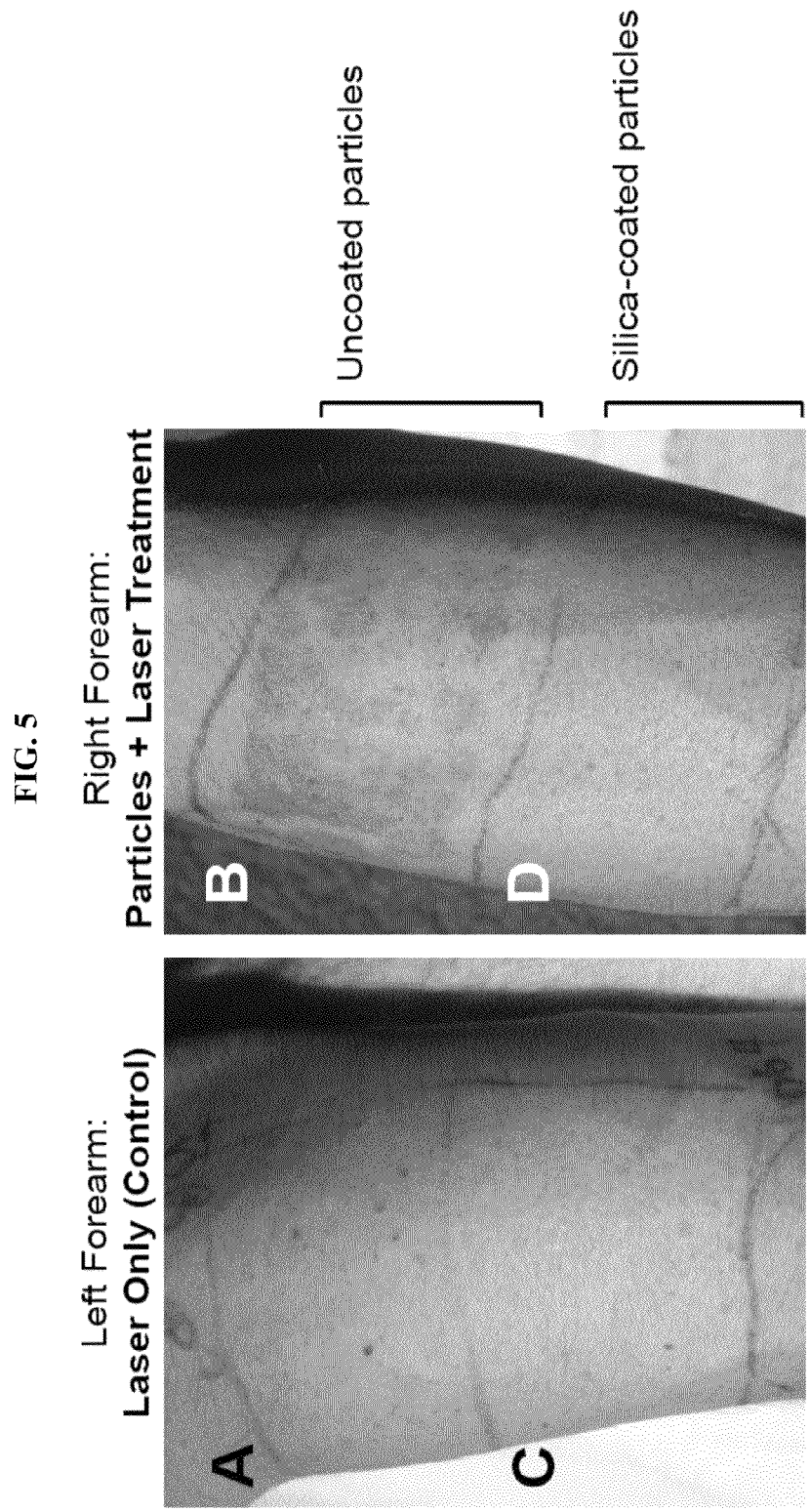
FIG. 5 depicts clinical observations in live human skin treated with Laser Only (left forearm) or Plasmonic Particles+Laser (right forearm) demonstrates non-specific and specific photothermal damage. (A,B) In the top panel, human skin was irradiated with 810 nm laser pulses (30 J/cm2, 30 ms, 2 passes) alone (A), or after treatment with a formulation of 830 nm resonant, Uncoated plasmonic nanoparticles in 20% propylene glycol (B). The plasmonic nanoparticle formulation was applied with 3 minute massage, and the skin surface wiped with 3 applications of alternative water and ethanol before laser irradiation. At 30 minutes following laser irradiation, non-specific clinical burns were observed in B compared to A, due to significant photothermal heating of residual, Uncoated particles on the skin surface. (C,D) In the bottom panel, human skin was irradiated with 1064 nm laser pulses (40 J/cm2, 55 ms, 3 passes) alone (C), or after treatment with a formulation of 1020 nm resonant, Silica-coated plasmonic nanoparticles in 20% propylene glycol (D). The plasmonic nanoparticle formulation was applied with 3 minute massage, and the skin surface wiped with 3 applications of alternative water and ethanol before laser irradiation. At 30 minutes following laser irradiation, no evidence of burning of the skin or erythema was observed in D or C, as Silica-coated particles could be sufficiently wiped from the skin surface. Magnified photography of D showed specific photothermal damage (perifollicular erythema and edema) in the nanoparticle-targeted site.
Figure 6:
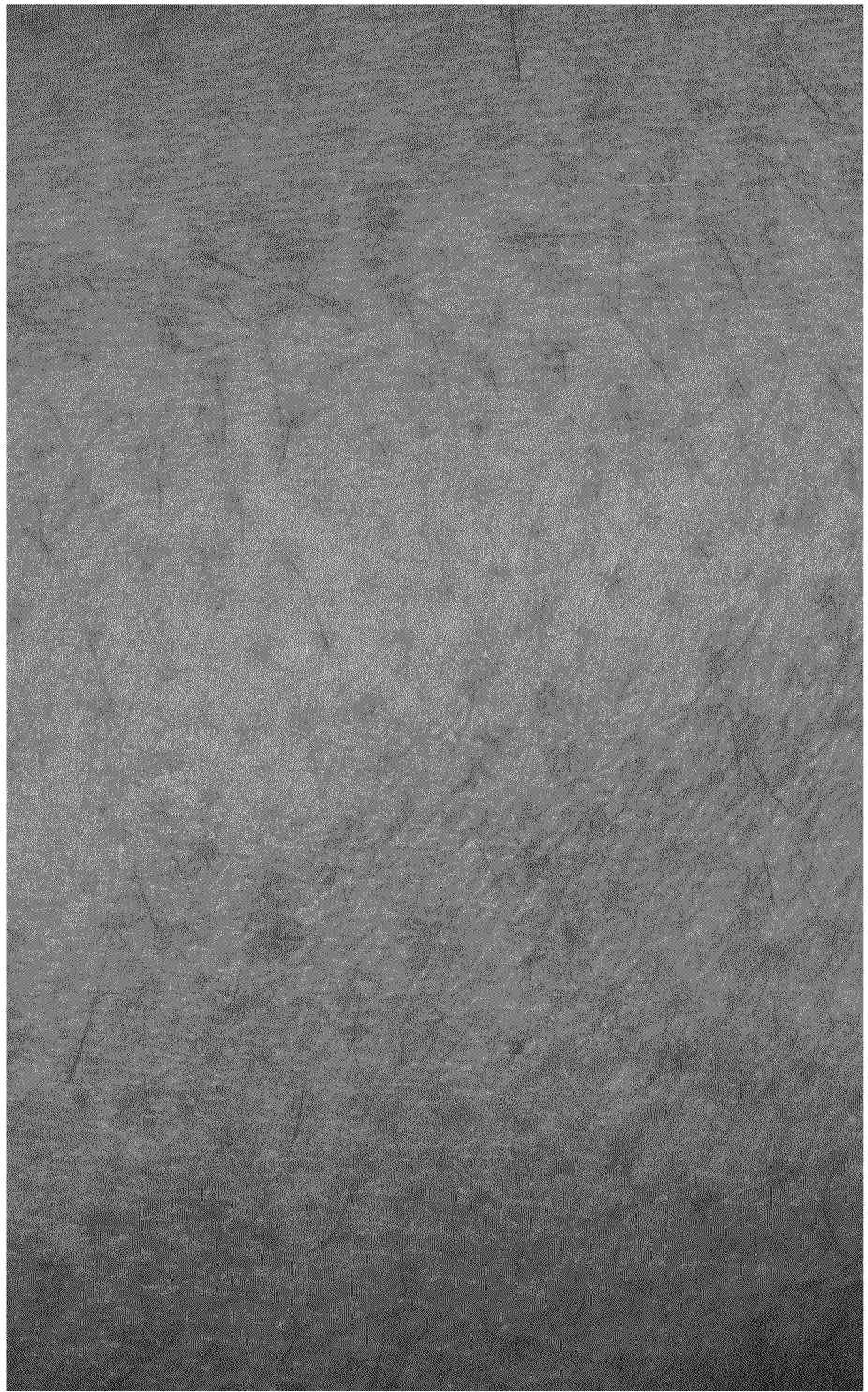
FIG. 6 is a photograph showing nanoparticle-targeted photothermal damage in live human skin treated with a plasmonic nanoparticle formulation and clinical laser. A formulation of 1020 nm resonant, silica-coated (200 nm-diameter) plasmonic nanoparticles in 20% propylene glycol and 3 minute massage was contacted with live human skin. The procedure was repeated 3 times, and skin surface wiped with 3 applications of alternating water and ethanol to remove residual particles. The treated skin was irradiated with 1064 nm laser pulses (40 J/cm$^2$, 55 ms, 3 passes). Following laser irradiation, clinical observation of perifollicular erythema and edema was visible at hair follicles where nanoparticles were targeted, but not visible in surrounding or non-particle-treated tissues.

Preferentially, a matrix component such as silica, polystyrene or polyethylene glycol is provided in the formulation to improve particle stability and enable facile removal from the skin surface after application and follicle targeting. Acetone, ethanol, or a debriding agent can be used to remove all particles from the surface of the skin that have not deposited in the follicle, in order to reduced or prevent non-follicular heating of the skin. In FIG. 5, live human skin was treated with Uncoated plasmonic particles compared to Silica-coated plasmonic particles, prior to laser-irradiation and comparison to no particle treatment (laser only) controls. Pre-treatment of skin, including shaving with razor and microdermabrasion (15 sec, medium setting) to remove hair-plugs and "open" the follicle for particle delivery, was performed on both forearms. Human forearm skin was irradiated with 810 nm laser pulses (30 $J/cm^2$, 30 ms, 2 passes) alone (FIG. 5A), or after treatment with a formulation of 830 nm resonant, Uncoated plasmonic nanoparticles in 20% propylene glycol (FIG. 5B). The plasmonic nanoparticle formulation was applied with 3 minute massage and repeated 3 times, and the skin surface wiped with 3 applications of alternative water and ethanol before laser irradiation. At 30 minutes following laser irradiation, non-specific clinical burns were observed due to significant photothermal heating of residual, Uncoated particles on the skin surface (FIG. 5B). Live human skin was also irradiated with 1064 nm laser pulses (40 $J/cm^2$, 55 ms, 3 passes) alone (FIG. 5C), or after treatment with a formulation of 1020 nm resonant, Silica-coated plasmonic nanoparticles in 20% propylene glycol (FIG. 5D). The plasmonic nanoparticle formulation was applied with 3 minute massage and repeated 3 times, and the skin surface wiped with 3 applications of alternative water and ethanol before laser irradiation. At 30 minutes following laser irradiation, no evidence of burning of the skin or erythema was observed, as Silica-coated particles could be sufficiently wiped from the skin surface (FIG. 5D). Magnified photography of the skin area treated with Silica-coated particles+Laser shows specific photothermal damage (perifollicular erythema and edema) in the nanoparticle-targeted site, without damage to surrounding or non-particle-treated tissues (FIG. 6).

Example 4

Use of Plasmonic Nanoparticles for Acne Treatment

Provided herein are methods for using the compositions described herein for the treatment of acne vulgaris and other acnes and acne-like skin conditions, but the selective targeting of sebaceous follicles, particularly the sebaceous glands and/or hair follicles. Plasmonic nanoparticles generated and formulated as described above are introduced into a target tissue region, generally a skin region, and activated with laser-based systems as known in the art in order to achieve effective hair removal.

To achieve maximal penetration depth and concentration of plasmonic nanoparticles in the hair follicle and/or near components of the sebaceous gland including the sebaceous duct, the sebum, the epithelial linking of the sebaceous gland, and/or near the bulge region including the stem cells, stem cell niche, epithelial lining of the bulge region, and/or near the follicular bulb, an optimal particle size of 100-800 nm containing one or several plasmonic nanoparticles is constructed. Nanoparticles encapsulating plasmonic nanoparticles can be formulated from any number of polymers or matrices. In some embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Preferentially, a matrix component such as silica, polystyrene or polyethylene glycol is provided in the formulation to improve particle stability and enable facile removal from the skin surface after application and follicle targeting. Preferentially, formulations include surfactants (e.g. sodium dodecyl sulfate, sodium laureth 2-sulfate, ammonium lauryl sulfate, sodium octech-1/deceth-1 sulfate), components of a lipid bilayer, a liposome, or a microsome. Surfactants disrupt the epidermal skin barrier, emulsify sebum, improve mixing of hydrophilic nanoparticles with hydrophobic solutions, and reduce entropic barriers to delivering hydrophilic particles to hydrophobic regions of the skin (e.g. between the hair shaft and surrounding sheath or follicle). Plasmonic nanoparticles including nanorods, nanoshells, nanospheres, or nanorice can be encapsulated within the polymer nanoparticle or matrix or deposited on the particle surface. Alternatively, nanoparticles in the size range of 100-250 nm, 250-500 nm, 800 nm-1500 nm, or greater than 1500 nm can be used.

The use of physical or thermal force amplifies or expedites the penetration of light absorbing nanoparticles and conjugates thereof into hair follicles and/or sebaceous glands, in part by causing dilation of the hair follicle prior to application of the nanoparticles. For example, ultrasound and other sonic forces, mechanical vibrations, hair shaft manipulation (including pulling), physical force, thermal manipulation, and other treatments are utilized to improve entry of light-absorbing nanoparticles into hair follicles and/or sebaceous glands. Nanoparticle formulation treatments are performed alone, in combination, sequentially or repeated 1-24 times.

Prior to application of the plasmonic nanoparticles, a pre-treatment step of removing excess sebum from the surface of the skin may be performed using chemical and/or mechanical means. Pre-treatment of skin with mechanical or chemical exfoliation is used in some embodiments to remove hair-plugs and "open" the follicle for particle delivery. Additionally, hairs can be shaven or waxed to create a void in the hair follicle for particles to fill.

An applicator is used to uniformly apply the composition of nanoparticles into follicles. The applicator can be a sponge, a cloth, direct contact from a finger, a tube, a syringe, a device that applies suction, an aerosol, a spray, or other means known in the art. In one example, a formulation of 1 ml of plasmonic nanoparticles at a concentration of 100 O.D. with peak resonance of 810 nm is applied to approximately 200 cm$^2$ area of the skin of an adult human subject with a syringe. A cloth is used to evenly distribute solution across the skin area and into the hair follicles. Massage from a mechanical vibrator for 2 minutes with or without ultrasound at 1 MHz for 5 minutes is applied to drive particles deep into the follicle. Particles penetrate ~50% down the full length of the hair shaft at concentrations sufficient to heat skin in a 100 um radius at incremental temperatures of 5-20-fold greater than is generated in similar volumes of adjacent skin when irradiated by a Diode (810 nm) laser. Acetone, ethanol, or a debriding agent can be used to remove all particles from the surface of the skin that have not deposited in the follicle, in order to reduced or prevent non-follicular heating of the skin.

Delivery of Plasmonic Nanoparticles to the Sebaceous Gland Determined Using Human Abdominoplasty Skin and Dark Field Imaging.

Figure 7:
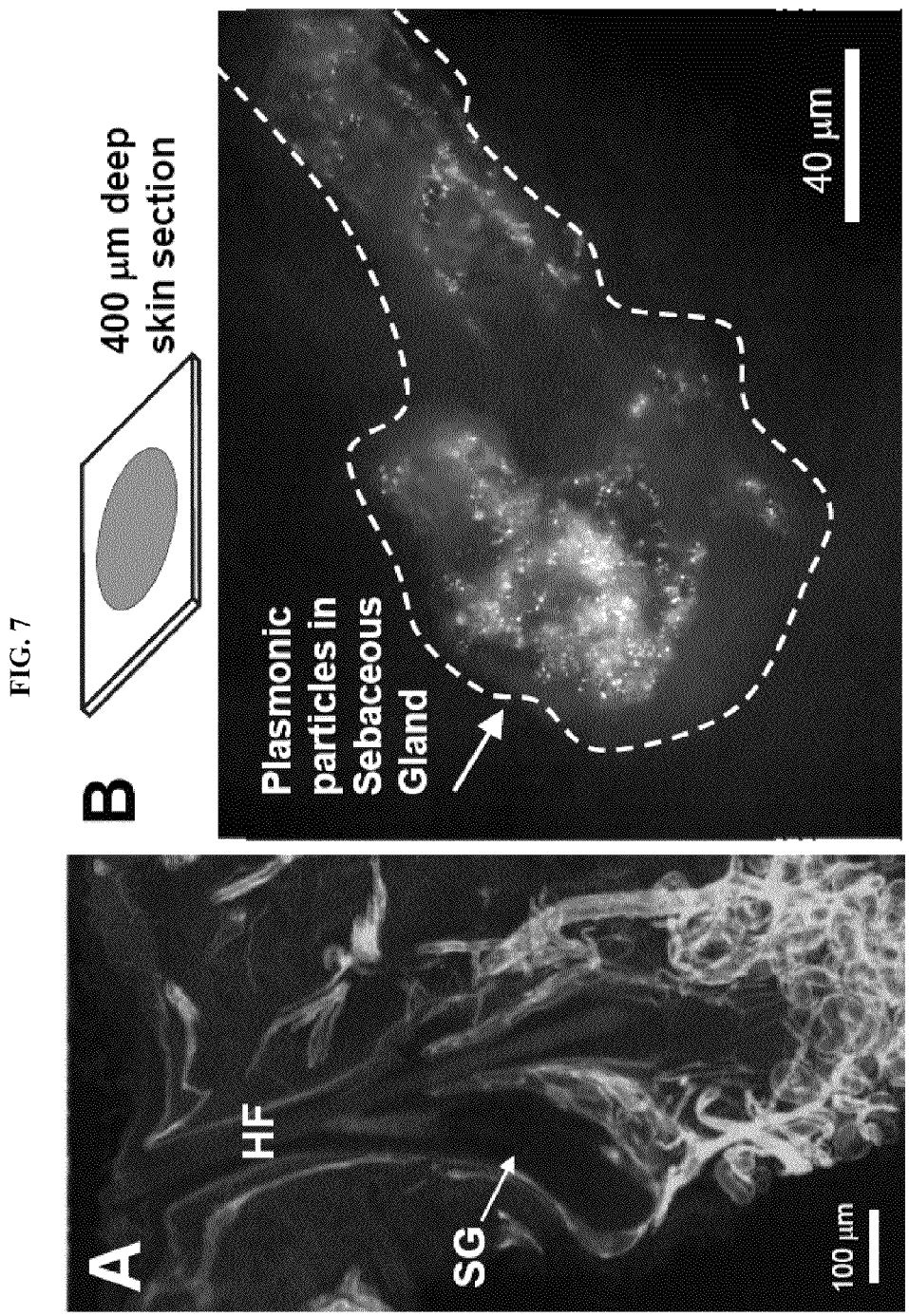
FIG. 7 is illustrative of a plasmonic nanoparticle formulation delivery to human skin sebaceous gland. (A) Confocal microscope image of a human skin biopsy and section, immunostained for Collagen IV basement membrane (blue) and PGP 9.5 nerve marker (green), shows hair follicle (HF) and sebaceous gland (SG) microanatomy. Red is silica nanoparticles (200 nm). (B) Schematic and dark field microscope image of excised human skin treated with plasmonic nanoparticle formulation, then sectioned and imaged horizontal to the follicle. Bright blue plasmonic particles are visible up to 400 μm deep and within the human sebaceous gland.

The human sebaceous gland exists within the pilosebaceous unit consisting of the hair, hair follicle, arrector pili muscle and sebaceous gland. In FIG. 7A, a human skin biopsy is immunostained with antibodies against Collagen IV (basement membrane marker, blue) and PGP 9.5 (nerve marker, green) to visualize representative pilosebaceous unit microanatomy, including the hair follicle (HF), sebaceous gland (SG) and arrector pili muscle. To deliver nanoparticles to the hair follicle and sebaceous gland, skin was first pre-treated with shaving to remove extruding hair, microdermabrasion (15 sec, medium setting) to remove hair-plugs and corneocytes, and chemical depilation to "open" follicle microwells for particle delivery. A 100 O.D. suspension of plasmonic nanoparticles (200 nm diameter), formulated in 1% sodium dodecyl sulfate (SDS) and 20% propylene glycol (PG) was contacted with excised human abdominoplasty skin, after which excess nanoparticle suspension was removed and manual massage performed for three minutes, followed by ultrasound (1 MHz) for 5 minutes. The procedure was repeated for a total of 3 applications, and surface residue removed with 3-5 applications of alternating water and ethanol. The skin sample was excised, fixed, sectioned along horizontal planes and subjected to dark field imaging. As assessed by dark field imaging of horizontal skin sections, compositions of plasmonic nanoparticles with a cosmetically acceptable carrier of 1% SDS/20% PG administered with massage and ultrasound can be delivered 400-600 μm deep into the human follicle and specifically into the sebaceous gland (FIG. 7B).

Cosmetic Formulations for Follicle and Sebaceous Gland Delivery in Human Skin.

Figure 8:
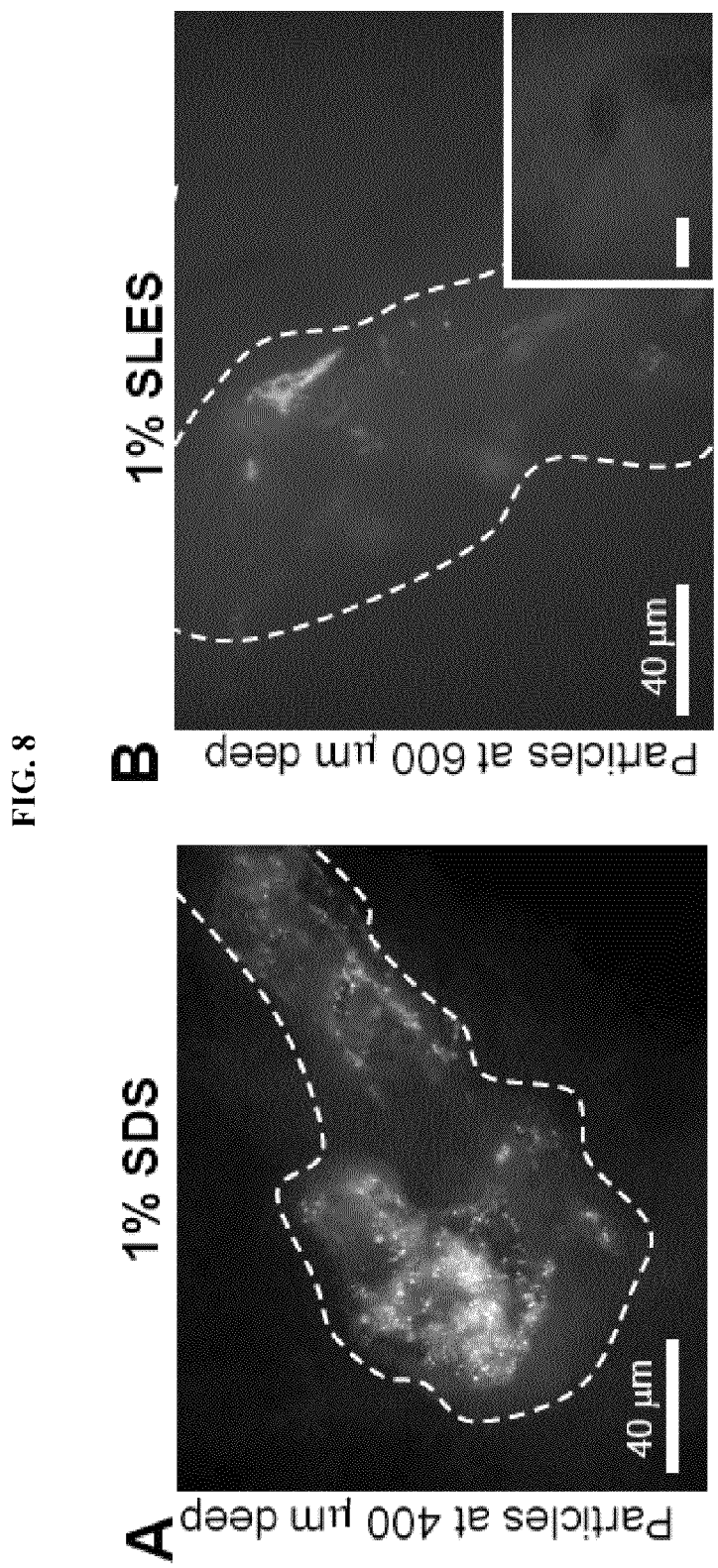
FIG. 8 is illustrative of cosmetic formulations of plasmonic nanoparticles for sebaceous gland targeting that include surfactants. Silica-coated nanoparticles (200 nm diameter, 100 O.D.) were formulated in 20% propylene glycol with the addition of surfactants sodium dodecyl sulfate (SDS) or sodium laureth-2 sulfate (SLES), applied to human skin with massage+ultrasound, and skin was sectioned in horizontal planes for dark field microscopy. (A) Formulations of plasmonic particles in 1% SDS/20% PG penetrated sebaceous gland down to 400 um as in FIG. 7. (B) Formulations of plasmonic particles in 1% SLES/20% PG penetrated sebaceous gland down to 600 um. Inset shows a skin section without visible particles (scale bar 40 um). Sebaceous gland is pseudo-outlined.

Preferentially, formulations include surfactants (e.g. sodium dodecyl sulfate, sodium laureth 2-sulfate, ammonium lauryl sulfate, sodium octech-1/deceth-1 sulfate), components of a lipid bilayer, a liposome, or a microsome. Surfactants disrupt the epidermal skin barrier and emulsify the sebum to enable improved mixing of hydrophilic nanoparticles in hydrophobic solutions. Humectants such as propylene glycol are used to help improve topical viscosity and maintain physiological pH. To demonstrate the efficacy and mechanism of exemplary cosmetic formulations for human sebaceous gland delivery, skin was first pre-treated with shaving to remove extruding hair, micro dermabrasion (15 sec, medium setting) to remove hair-plugs and corneocytes, and chemical depilation to "open" follicle microwells for particle delivery. Two separate 100 O.D. suspensions of plasmonic nanoparticles (200 nm diameter) were formulated in 1% sodium dodecyl sulfate and 20% propylene glycol (SDS/PG) or in 1% sodium laureth-2-sulfate and 20% propylene glycol (SLES/PG). Formulations were contacted with two separate excised human abdominoplasty skin samples, and massage for 3 minutes followed by ultrasound (1 MHz) for 5 min was performed to drive particles deep into the follicles. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of plasmonic nanoparticles with a cosmetically acceptable carrier of 1% SLES/20% administered with massage and ultrasound can be delivered 400-600 μm deep into the human follicle and specifically into the sebaceous gland (FIG. 8B).

Impact of Massage vs. Ultrasound on Nanoparticle Delivery to Human Follicles and Sebaceous Gland.

Figure 9:
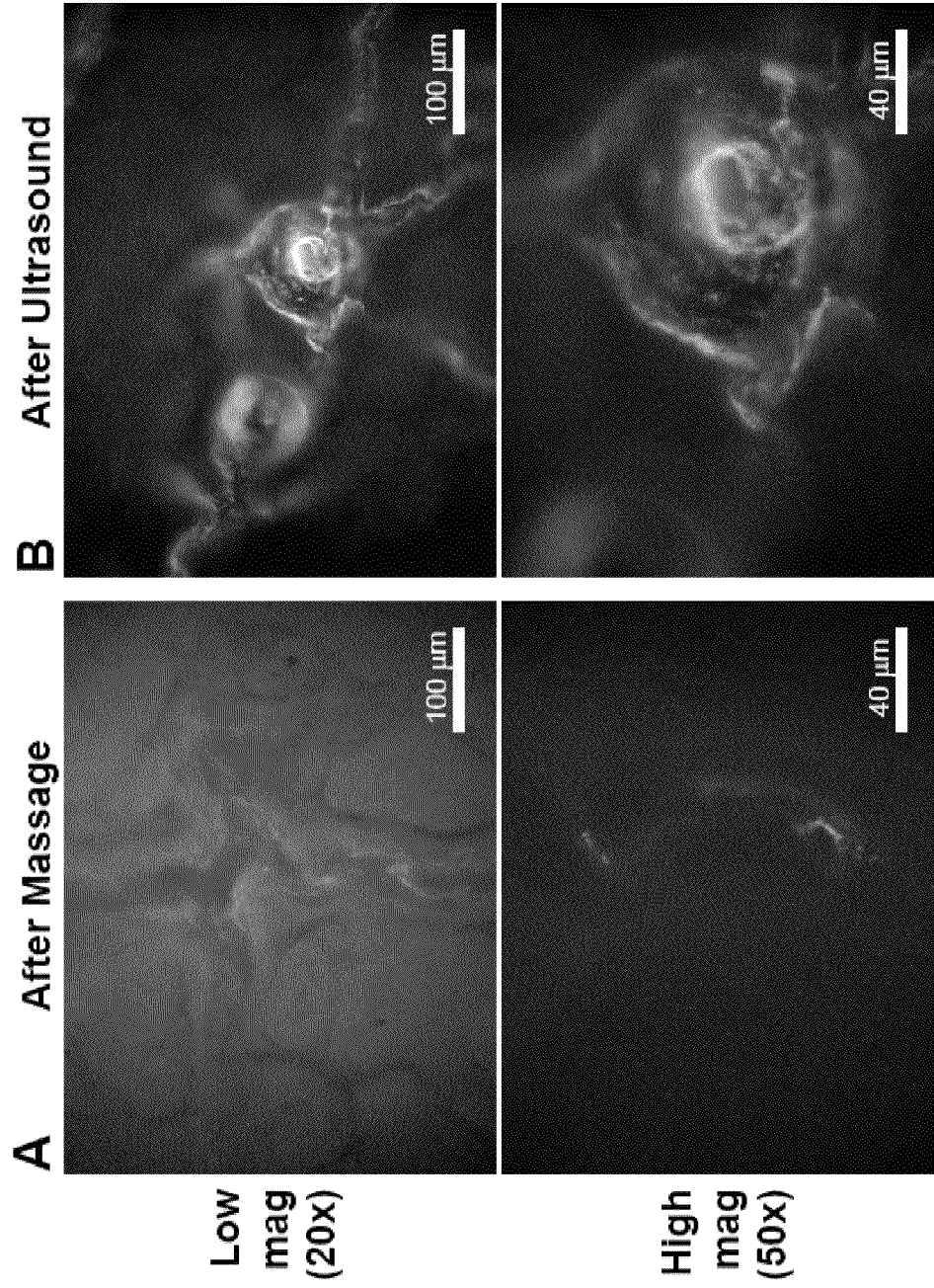
FIG. 9 is an image depicting impact of massage vs. ultrasound on nanoparticle targeting to the human follicle and sebaceous gland. Silica-coated nanoparticles (200 nm diameter, 100 O.D.) were formulated in 1% SDS/20% propylene glycol and applied to human skin with massage or ultrasound. Dark field images of horizontal planar sections taken at low (20x) and high (50x) magnification show (A) little to no accumulation of plasmonic particles into follicle infundibulum after massage alone, compared to (B) follicle infundibulum expansion and significant plasmonic particle accumulation after ultrasound alone.

Ultrasound and other sonic forces, mechanical vibrations, hair shaft manipulation (including pulling), physical force, thermal manipulation, and other treatments are utilized to improve entry of light-absorbing nanoparticles into hair follicles and/or sebaceous glands. Mechanical massage improves follicular penetration through hair shaft 'pumping' mechanisms, while ultrasound enhances transdermal drug delivery through temporary disruption of the skin's lipid bilayer, bubble formation, and liquid microstreaming. To characterize the effects of massage decoupled from ultrasound, skin was first pre-treated with shaving to remove extruding hair, micro dermabrasion (15 sec, medium setting) to remove hair-plugs and corneocytes, and chemical depilation to "open" follicle microwells for particle delivery. A 100 O.D. suspension of plasmonic nanoparticles (200 nm diameter), formulated in 1% sodium dodecyl sulfate (SDS) and 20% propylene glycol (PG), was contacted with three separate excised human abdominoplasty skin samples. In the three treated human skin samples, massage only was performed for 3 minutes, ultrasound only (1 MHz) was performed for 5 minutes, or massage followed by ultrasound was performed to drive particles deep into the follicles. In a fourth sample, no particles were applied to skin. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of plasmonic nanoparticles with a cosmetically acceptable carrier of 1% SLES/20% administered via ultrasound deliver more plasmonic nanoparticles to the infundibulum versus massage, albeit both mechanisms facilitate delivery (FIG. 9).

Additional Plasmonic Nanoparticle Formulations for Follicle and Sebaceous Land Deliver in Human Skin.

Figure 10:
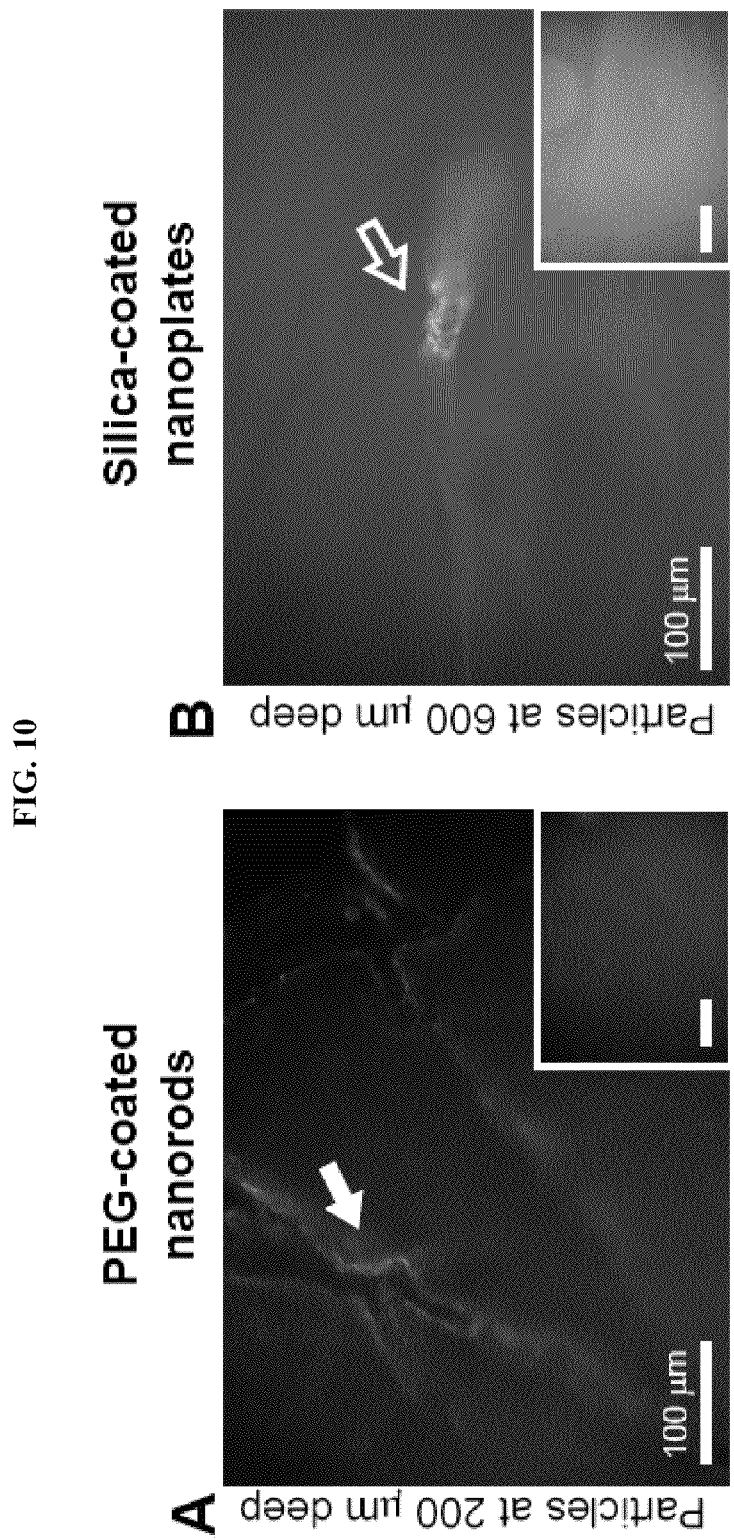
FIG. 10 depicts an embodiment of the plasmonic nanoparticle cosmetic formulations for sebaceous gland targeting. Plasmonic nanoparticles comprising different shapes and coatings were formulated in 1% SDS/20% propylene glycol and applied to human skin with massage+ultrasound, and skin was sectioned in horizontal planes for dark field microscopy. (A) Polyethylene glycol (PEG)-coated nanorods (gold, 15×30 nm dimension) were observed within the follicle infundibulum up to 200 um deep (white arrow). (B) Lower concentration (10 O.D.) Silica-coated nanoplates (silver, 200 nm diameter) were observed up to 600 um deep in the follicle and in the sebaceous gland (open arrow). Inset shows skin sections without visible particles (scale bar 100 um).

In some embodiments, plasmonic nanoparticles include nanorods, nanoshells, nanospheres, or nanorice, or plasmonic nanoparticles encapsulated within the polymer nanoparticle or matrix or deposited on the particle surface. Preferentially, a matrix component such as silica, polystyrene or polyethylene glycol is provided in the formulation to improve particle stability and enable facile removal from the skin surface after application and follicle targeting. To demonstrate the formulation of additional plasmonic nanoparticle shapes and concentrations for follicle, infundibulum, and sebaceous gland delivery, skin was first pre-treated with shaving to remove extruding hair, microdermabrasion (15 sec, medium setting) to remove hair-plugs and corneocytes, and chemical depilation to "open" follicle microwells for particle delivery. Separately, 10 O.D. suspensions of Silica-coated nanoplates, 30 O.D. suspensions of polyethylene-glycol coated plasmonic nanorods, and fluorescent silica particles were formulated in 1% sodium dodecyl sulfate and 20% propylene glycol. Formulations were contacted with three separate excised human abdominoplasty skin samples, and massage for 3 minutes followed by ultrasound (1 MHz) for 5 min was performed to drive particles deep into the follicles. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of Polyethylene glycol (PEG)-coated nanorods (gold, 15×30 nm dimension) in cosmetically acceptable carrier, administered via ultrasound and massage, were observed within the follicle infundibulum at 200 um deep (FIG. 10A). Compositions of plasmonic nanoparticles (Silica-coated nanoplates) at lower concentration (10 O.D.), were apparent at 400-600 um deep in the follicle and in the sebaceous gland (open arrow), albeit at lower concentration than comparable particles in a similar cosmetic carrier at 100 O.D (FIG. 10B).

Assessment of Photothermal Destruction of Sebaceous Gland and Tare Targeted Skin Structures.

Nanoparticle formulations are tested in ex vivo animal skin samples, ex vivo human skin samples, and in vivo human skin as described in Example 3. One can measure efficacy of photothermal destruction at the nanoparticle accumulation site by measuring thermal damage to sebocytes and reduction in sebum production in the treated sebaceous follicles. To assess photothermal destruction, human skin is first pre-treated with shaving to remove extruding hair, micro dermabrasion (15 sec, medium setting) to remove hair-plugs and corneocytes, and chemical depilation to "open" follicle microwells for particle delivery. Skin is contacted with a 100 O.D. suspension of 810 nm resonant plasmonic nanoparticles (200 nm diameter), and is massaged for 3 minutes followed by ultrasound (1 MHz) for 5 min to drive particles deep into the follicles. The procedure is repeated for a total of 3 applications, and surface residue removed with 3-5 applications of alternating water and ethanol. Treated human skin samples are laser irradiated with 810 nm laser (40 J/cm$^2$, 30 ms, 5 pulses), and compared to laser only treated human skin. Human skin is biopsied, fixed in Zamboni's solution with 2% picric acid, and cryosectioned by freezing sliding microtome. Slides with mounted paraffin sections are deparaffinized and stained with hematoxylin and eosin (H&E). Histological sections are examined at various depths for markers of thermal damage and inflammation. Hematoxylin and eosin (H&E) is used to image skin and follicle microanatomy and indicate degeneration of hair shafts, atrophy of sebaceous glands, and cell vacuolization (indicating cellular damage). Nitro blue tetrazolium chloride (NBTC), a lactate dehydrogenase stain that is lost upon thermal injury to cells, may also be used to assess damage to keratinocytes vs. sebocytes. An intracellular stain, Oil-Red-O, may be used to determine lipid and sebum oil content in treated samples. Sebum excretion rates are measured on in vivo skin at 1-3 months follow up using sebum-absorbant tapes to demonstrate functional change in sebum flow. Clearance and prevention of acne lesions is measured by patient reported outcomes and counting acne lesions at 1-3 months follow up.

Example 5

Formulation of Thermoablative Plasmonic Nanoparticles for Vascular Ablation

Formulations are prepared to maximize nanoparticle stability (degree of aggregation in solution), nanoparticle concentration, and nanoparticle absorbance (degree of laser-induced heating at different concentrations) once injected into the blood stream. Nanoparticles are generated as in Example 1 using an appropriate solvent. The mixture comprising a plurality of nanoparticles in water is concentrated to about 100-500 OD at peak absorbance and exchanged for a new solvent by liquid chromatography, a solvent exchange system, a centrifuge, precipitation, or dialysis. Typical exchange solvent is 0.15 mol/L NaCl, 0.1 mol/L Na phosphate buffer (pH 7.2).

Example 6

Use of Plasmonic Nanoparticles for Thermoablation of Component(s) of Vessels and Microvessels Nanoparticle-containing compositions are administered, typically intravascularly. Subsequent to such administration of plasmonic nanoparticles, a laser matched to the peak plasmonic resonance of the particles (e.g., 755 nm, 810 nm, or 1064 nm) is applied to heat nanoparticles and surrounding tissue. Pulse widths of 10-100 ns, 100 ns-1 ms, 1-10 ms, 10-100 ms, 100-1000 ms or continuous wave irradiation is used to achieve thermal heat gradients and localized heating in the vicinity of particle or particles of 20-200 nm. 200 nm-2 µm, 2-20 µm, 20-200 µm, 200 µm-2 mm. Thermal gradients of 20-200 nm are achieved from individual particles. Supra millimeter thermal gradients are achieved by the collective heat deposition of many particles in veins with diameters of several hundred microns or more. Irradiation is applied from 1 pulse to many pulses over seconds to minutes. A cooling device for epidermal layers is used concomitant to irradiation to reduce pain and prevent thermal damage elsewhere. Laser position, fluence, wavelength, angle of incidence, pattern of irradiation is modified to achieve irradiation of vessels at specific depths between 0-10 mm, while avoiding heating of non-target vasculature. Alternatively, laser or light is administered through fiber optic waveguide administered via a catheter to heat the particles in larger veins.

In one embodiment a flank of the tissue is irradiated with 2 W/cm$^2$, 810 nm, 1 cm beam diameter after injection of PEG-nanorods with peak plasmon resonance at 810 nm. Thermographic imaging is used to assess surface temperature of tissue immediately after irradiation.

Assessment of thermal damage to component(s) of vessels, microvessels, or capillaries. Thirty minutes after application, target vessels and the surrounding supporting tissue (e.g. skin) are removed. Biopsies are fixed in 10% paraformaldehyde, paraffin-embedded, and cut into 5-um sections on a microtome in transverse directions. Slides with mounted paraffin sections are deparaffinized and stained with hematoxylin and eosin (H&E) or silver enhancement staining. Using H&E staining and light microscopy, one or several vessels, microvessels, and capillaries can be imaged. Scoring is performed for visible thermal damage of the vessel structures. Additionally, vessel staining (e.g. CD31 stain) is performed to clearly identify vascular structures within tissue samples.

Example 7

Determination of Efficiency of Conversion of Light to thermal Energy

Figure 11A:
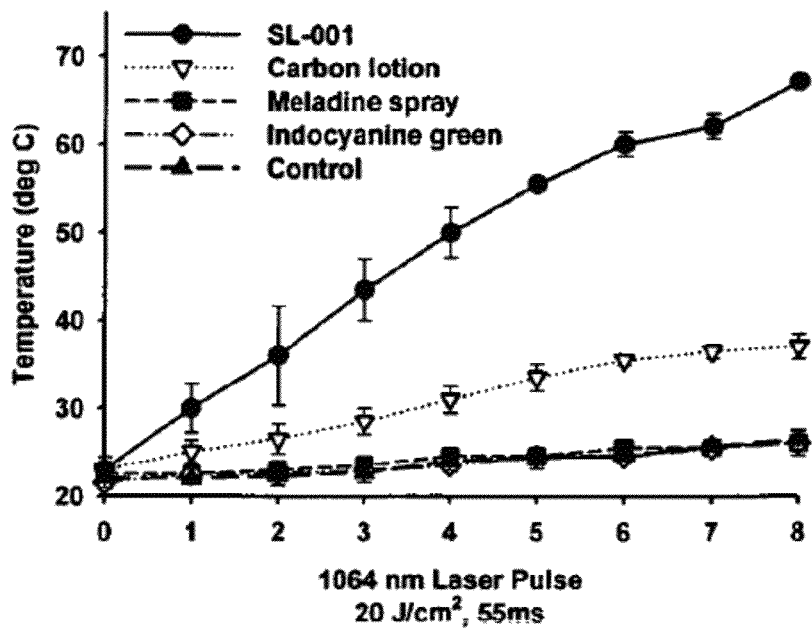
FIG. 11A is illustrative of temperature profiles of certain embodiments of plasmonic nanoparticle formulations compared to other commercial and research chromophores.
Figure 11B:
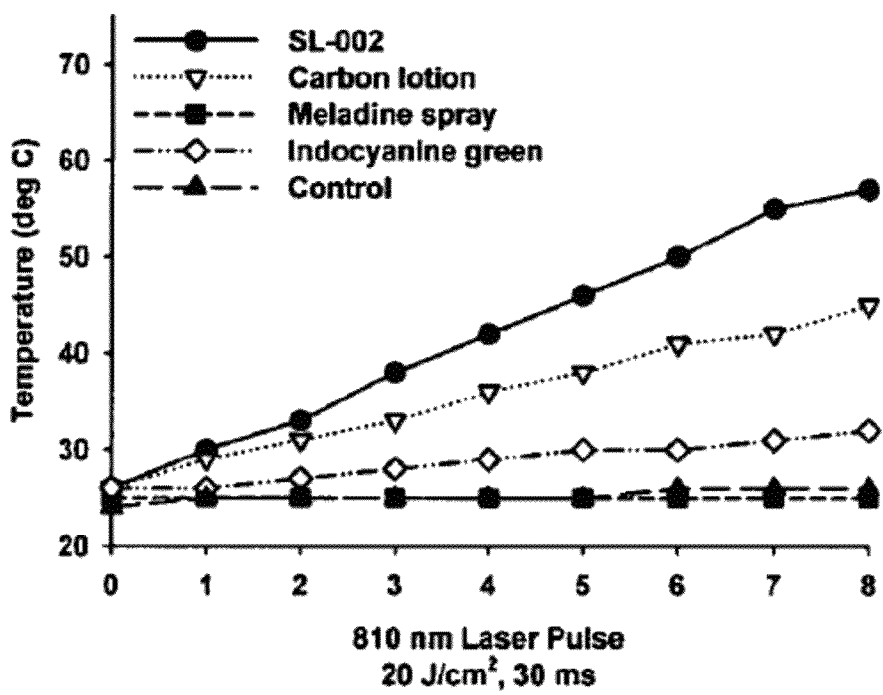
FIG. 11B is illustrative of temperature profiles of certain embodiments of plasmonic nanoparticle formulations compared to other commercial and research chromophores.

A suspension of plasmonic nanoparticles (silica-coated nanoplates having a diameter of about 100-200 nm, as described here) was prepared by formulating the plasmonic nanoparticles in 20% propylene glycol in water to a concentration of about 1000 O.D., and the ability of this suspension to convert laser light to thermal energy was determined. Available commercial and research products, e.g., stock solutions of carbon lotion (20-200 mg/ml carbon, TelsarSoft-Light), Meladine spray (1 mg/ml melanin, Creative Technologies), Indocyanine green (5 mg/ml in water, Sigma Aldrich), and vehicle control (20% propylene glycol in water) were also tested. All solutions were diluted 1:1000 from their indicated stock solution concentration, loaded at 90 µl per well into a 96-well plate, and baseline temperatures were measured by K thermocouple with micrometer (ExTech Instruments, Waltham Mass.) and recorded. Solutions were then irradiated with repeated laser pulses at various wavelengths (e.g., 1064 nm, 810 nm, and 755 nm), fluence (e.g., 10, 20, and 30 J/cm2) and pulse sequence parameters (e.g., 30 ms and 55 ms). Following each sequential laser pulse, up to a total of 8 pulses, solution temperatures were measured and recorded. As shown in FIGS. 11A-11B, a series of plasmonic nanoparticle (PNP) formulations (labeled SL-001 and SL-002) exhibited ultra-high absorption compared to existing commercial and research chromophores. (FIGS. 11A, B) Rate of temperature increase over sequential laser pulses for PNP formulation SL-001 (FIG. 11A, closed circle), resonant at 1064 nm laser wavelength, upon irradiation with 1064 nm laser (A), and SL-002 (FIG. 11B closed circle), resonant at 810 nm laser wavelength, upon irradiation with 810 nm laser (B). Control solutions are as follows: Carbon lotion (open triangle), Meladine spray (closed square), Indocyanine green (open diamond), and 20% propylene glycol (closed triangle). All solutions were diluted 1:1000 from stock clinical concentration for laser irradiation and temperature measurements. For A, n=2 and error bars are s.d. of the mean.

Example 8

Figure 12A:
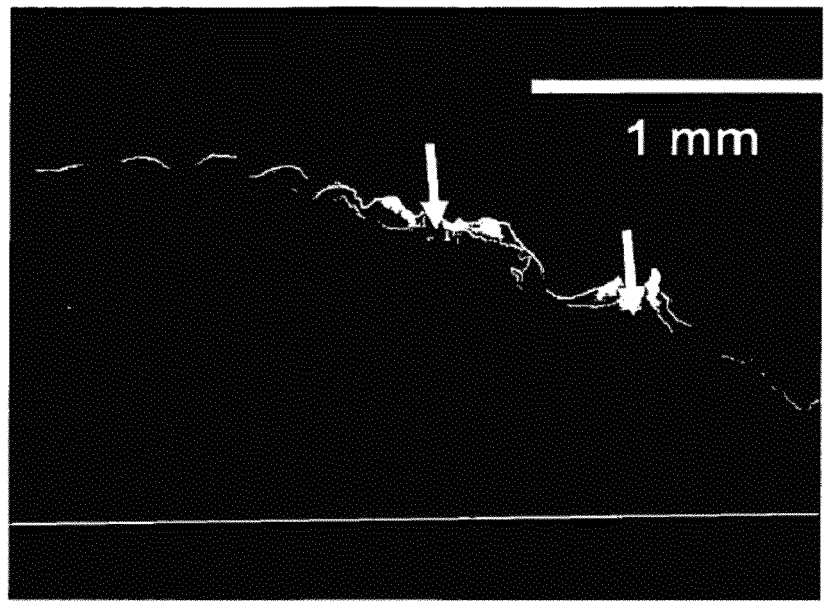
FIGS. 12A and 12B are images of embodiments of nanoparticle formulations in porcine skin.
Figure 12B:
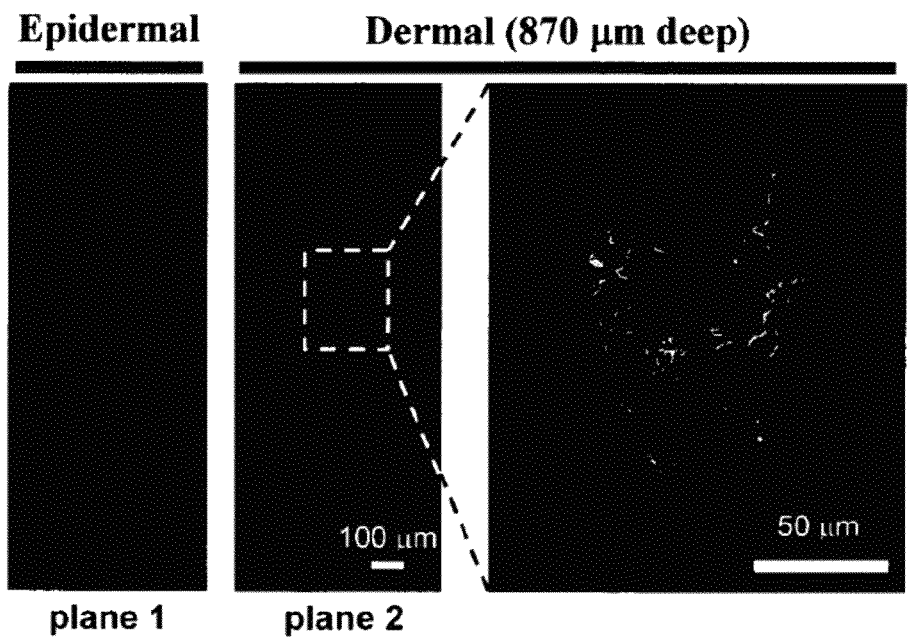

Quantitation of nanoparticle delivery into target tissues. Red fluorescent nanoparticles (Corpuscular Inc., Cold Spring, N.Y.) were contacted with isolated porcine skin explants as follows. A 2.5 mg/ml solution of $SiO_2$, 200 nm diameter, 548 nm emission particles in 20% propylene glycol was pipetted onto the skin surface and mechanically massaged into the tissue explant. An ethanol wipe was used to remove non-penetrating particles. As shown in FIGS. 12A-12B, the provided formulations of nanoparticles (NPs) deeply and specifically penetrate ex vivo porcine skin. FIG. 12A demonstrates representative survey fluorescence image of porcine skin, treated with red fluorescent NPs and histologically sectioned. Red (light contrast) NPs are imaged after penetrating the hair follicle infundibulum (arrows) and deep follicle, but not in the underlying dermis. FIG. 12B shows representative confocal images show red NPs within superficial and deep follicle (−870/−tm) at high and low magnification. Green (dark contrast) is tissue autofluorescence (488 nm emission). Scale bars as labeled 1 mm (A), 10 µm (B, left), 50 µm (B, right).

Figure 13A:
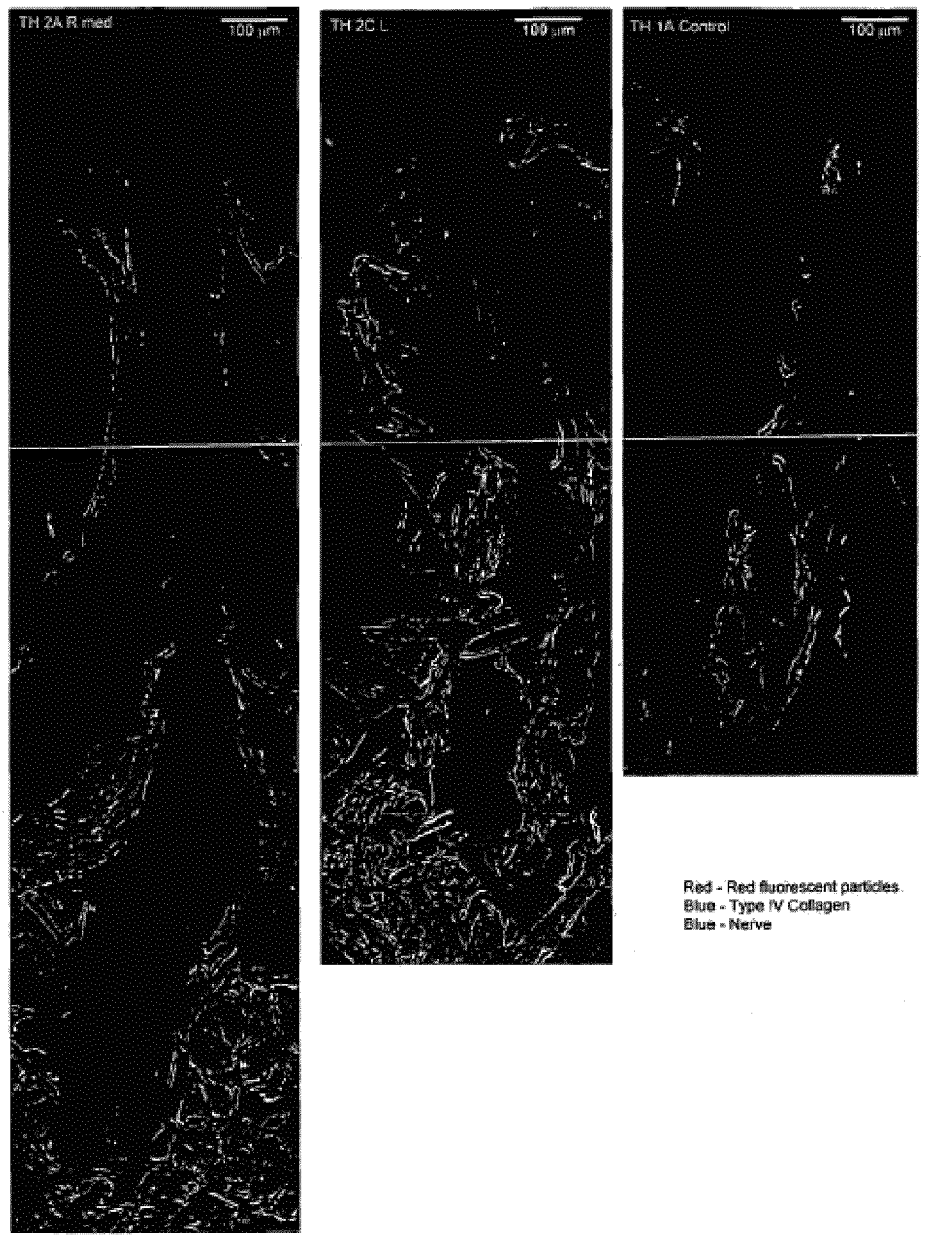
FIGS. 13A and 13B are images of biopsies taken from in vivo-treated human skin, which were sectioned and immunostained for skin markers, with various embodiments of nanoparticles.
Figure 13B:
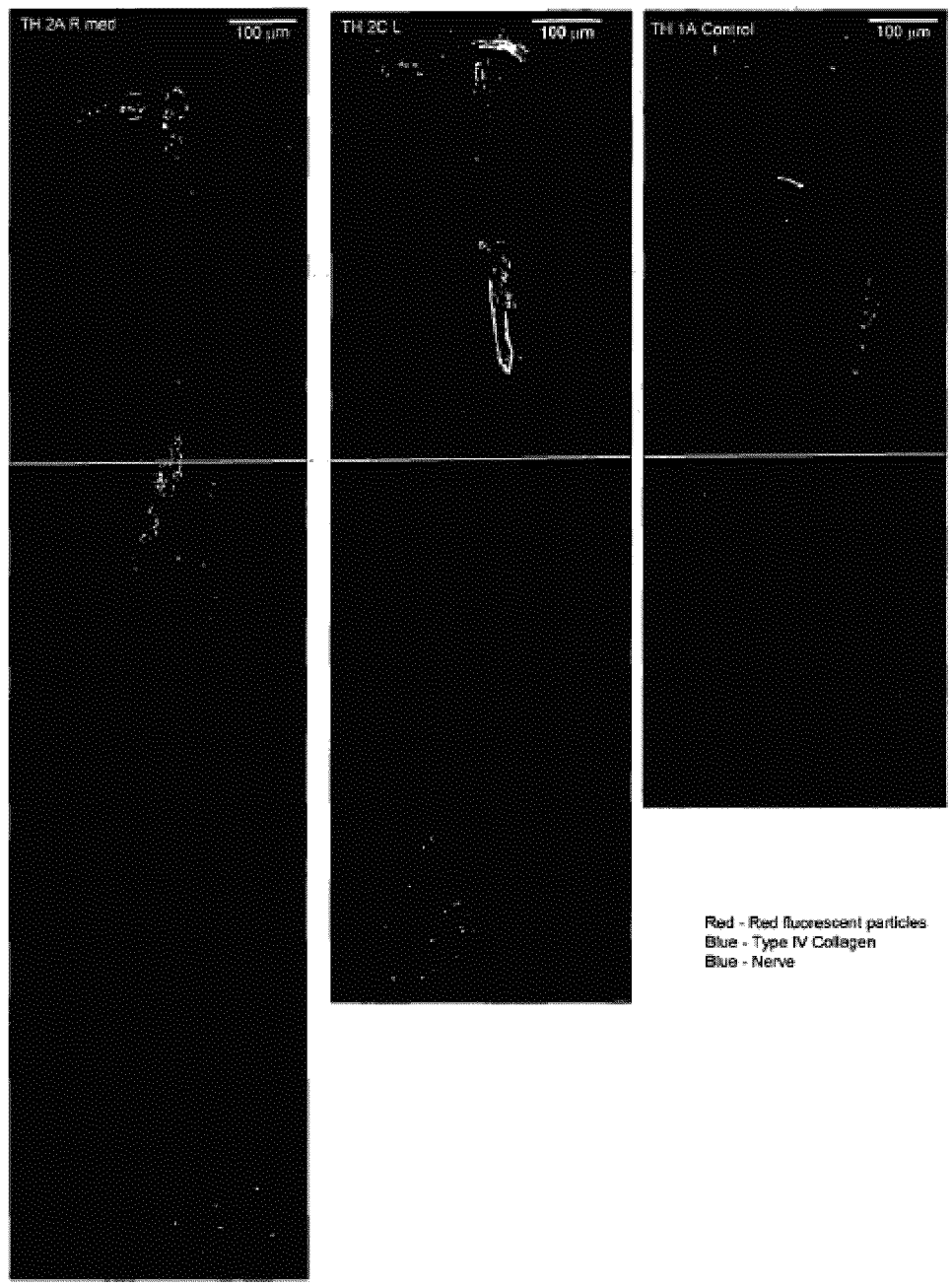

Further, formulations of nanoparticles (NPs) with silica coating deeply and specifically penetrate in vivo human skin. A region of an upper arm of a male human subject having skin Type 3 was treated with the red nanoparticles essentially as described above. Shown in FIGS. 13A and 13B are representative confocal images of biopsies taken from the in vivo-treated human skin, which were sectioned and immunostained for skin markers. Left-'TH 2A R med' sample shows red hair follicle fluorescence after red NP application with massage, ultrasound, and no pre-depilation with waxing; Middle 'TH 2C L' sample shows red hair follicle fluorescence after red NP application with massage, ultration, and pre-depilation with waxing; Right-'TH 1A Control' shows background red autofluorescence of hair follicle. FIG. 13A is 3 color image where red is NPs, blue is collagen IV (staining basement membrane) and green is PGP 9.5 (staining nerve fiber). FIG. 13B shows red channel only in black and white. Scale bars as labeled 100 µm.

As will be understood by the skilled artisan, the subject matter described herein may be embodied in other specific forms without departing from the spirit or essential characteristics thereof. The foregoing embodiments are therefore to be considered in all respects illustrative rather than limiting on the invention described herein.

What is claimed is:

1. A method of localizing thermal damage to a hair follicle, comprising:
   applying a composition to a skin surface,
   wherein said composition comprises a plurality of unassembled plasmonic nanoparticles,
   wherein the unassembled plasmonic nanoparticles comprise a conductive metal portion,
   wherein the conductive metal portion comprises at least one of gold or silver,
   wherein the unassembled plasmonic nanoparticles have a size in a range of 10 nm to 300 nm,
   wherein the unassembled plasmonic nanoparticles comprise a coating that coats the conductive metal portion, wherein said coating facilitates selective removal from the skin surface;
   wherein the coating comprises at least one of silica or polyethylene glycol (PEG),
   wherein the unassembled plasmonic nanoparticles have a concentration of $10^9$ to $10^{23}$ particles per ml of the composition, wherein said concentration is sufficient to, after exposure to irradiation, induce thermal damage in the hair follicle;
   distributing the composition from the skin surface to the hair follicle to target the hair follicle;
   selectively removing the composition from the skin surface, while leaving the composition localized within the hair follicle; and
   irradiating the composition with an infrared light source thereby inducing a plurality of surface plasmons in said unassembled plasmonic nanoparticles,
   wherein the induction of the surface plasmons generates thermal damage to the hair follicle for at least one of hair removal or hair growth reduction.

2. The method of claim 1,
   wherein the conductive metal portion is a silver nanoplate, and
   wherein the coating is less conductive than the conductive metal portion.

3. The method of claim 1, wherein the unassembled plasmonic nanoparticles comprise an optical density of 10 O.D. to 5,000 O.D. at an infrared light range.

4. The method of claim 1, wherein the unassembled plasmonic nanoparticles comprise a solid, conducting silver core and a silica coating.

5. The method of claim 1, further comprising pre-treating the skin surface prior to irradiating the composition, wherein pre-treating the skin surface comprises at least one of the group consisting of: shaving, waxing, mechanical exfoliation, and chemical exfoliation.

6. The method of claim 1, wherein irradiating the composition comprises irradiating the hair shaft.

7. A method of localizing thermal damage to a hair follicle, comprising:
   topically applying a solution of unassembled plasmonic nanoparticles to a skin surface,
   wherein the unassembled plasmonic nanoparticles have a dimension in a range of 10 nm to 300 nm,
   wherein the unassembled plasmonic nanoparticles have a concentration of $10^9$ to $10^{23}$ particles per ml of the solution,
   wherein the unassembled plasmonic nanoparticles comprise a conductive metal portion,
   wherein the conductive metal portion comprises at least one of gold or silver,
   wherein the unassembled plasmonic nanoparticles comprise a coating that coats the conductive metal portion, wherein said coating facilitates selective removal from the skin surface;
   wherein the coating comprises at least one of silica or polyethylene glycol (PEG),
   targeting the hair follicle by redistributing the solution of unassembled plasmonic nanoparticles with a mechanical vibration device from the skin surface to a portion of a hair follicle;
   selectively removing the solution from the skin surface, while leaving the solution localized within the hair follicle; and
   irradiating the solution of unassembled plasmonic nanoparticles with an energy wavelength in a range of 750 nm to 1200 nm to induce a plurality of surface plasmons in said unassembled plasmonic nanoparticles, thereby localizing thermal damage to said hair follicle.

8. The method of claim 7, wherein the concentration of the unassembled plasmonic nanoparticles is $10^9$ to $10^{16}$ particles per ml of the solution.

9. The method of claim 7, wherein the unassembled plasmonic nanoparticles have an optical density of 10 O.D. to 5,000 O.D. within an infrared light range
   wherein the coating is less conductive than the conductive metal portion.

10. The method of claim 7, wherein the coating is semi-conductive, wherein the conductive metal portion is inside the coating, and wherein the coating is less conductive than the conductive metal portion.

11. A method of localizing thermal damage to a hair follicle, comprising:
    applying a solution of unassembled plasmonic nanoparticles to a skin surface,
    wherein the unassembled plasmonic nanoparticles comprise a conductive metal portion,
    wherein the conductive metal portion comprises at least one of gold or silver;
    distributing the solution of unassembled plasmonic nanoparticles from the skin surface to the hair follicle thereby targeting the hair follicle;
    wherein the unassembled plasmonic nanoparticles have a peak absorption wavelength of between 750 nm and 1200 nm,
    wherein the unassembled plasmonic nanoparticles have a concentration of $10^9$ to $10^{23}$ particles per ml of the solution,
    wherein the unassembled plasmonic nanoparticles have a size in the range of 10 nm to 300 nm,
    wherein the unassembled plasmonic nanoparticles comprise a coating that coats the conductive metal portion,
    wherein the coating comprises at least one of silica or polyethylene glycol (PEG),
    selectively removing the solution from the skin surface while leaving the solution localized within the portion of the hair follicle, and
    irradiating the solution of unassembled plasmonic nanoparticles with an energy to induce said unassembled plasmonic nanoparticles for generating localized thermal damage in the hair follicle.

12. The method of claim 11, further comprising:
    pre-treating the skin surface to increase delivery of the unassembled plasmonic nanoparticles to the hair follicle with at least one of the group consisting of shaving, waxing, peeling, cyanoacrylate surface peeling, a calcium thioglycolate treatment, a surface exfoliation, a mechanical exfoliation, a salt glow, a microdermabrasion, a chemical exfoliation, a chemical exfoliation with an enzyme, a chemical exfoliation with alphahydroxy acid, and a chemical exfoliation with betahydroxy acid;

wherein distributing the solution of unassembled plasmonic nanoparticles in contact with the hair follicle comprises distribution with a mechanical vibration device; and wherein irradiating the solution of unassembled plasmonic nanoparticles comprises exposing the solution of unassembled plasmonic nanoparticles to the energy wavelength of between 750 nm and 1200 nm to induce a plurality of surface plasmons in said unassembled plasmonic nanoparticles, thereby localizing thermal damage to said hair follicle.

13. The method of claim 11, further comprising:

wherein distributing the solution of unassembled plasmonic nanoparticles in contact with the hair follicle comprises distribution with a mechanical vibration device, wherein the mechanical vibration device comprises at least one of the group consisting of an ultrasound device and a massage device;

wherein irradiating the solution of unassembled plasmonic nanoparticles with the energy wavelength comprises an infrared light source of between 750 nm and 1200 nm to induce a plurality of surface plasmons in said unassembled plasmonic nanoparticles, thereby localizing thermal damage to said hair follicle.

14. The method of claim 11, wherein the unassembled plasmonic nanoparticles are nanoplates, wherein the unassembled plasmonic nanoparticles have an optical density of 10 O.D. to 5,000 O.D. within an infrared light range and the concentration is $10^9$ to $10^{18}$ particles per ml of the solution; and irradiating the solution of unassembled plasmonic nanoparticles with the energy wavelength of between 750 nm and 1200 nm to induce a plurality of surface plasmons in said unassembled plasmonic nanoparticles, thereby localizing thermal damage to said hair follicle.

15. The method of claim 11, wherein distributing the solution of unassembled plasmonic nanoparticles from the skin surface to the hair follicle comprises distribution with a mechanical vibration device, wherein the mechanical vibration device comprises at least one of the group consisting of an ultrasound device, a sonic force device, a massage device, a high pressure air flow device, a high pressure liquid flow device, and a vacuum device, and a dermabrasion device, and wherein selectively removing the solution from the skin surface comprises using water or alcohol to remove the solution from the skin surface while leaving the solution localized within the hair follicle.

16. The method of claim 1, wherein distributing the solution of unassembled plasmonic nanoparticles from the skin surface to a portion of the hair follicle comprises distribution with a mechanical vibration device, wherein the mechanical vibration device comprises at least one of the group consisting of an ultrasound device and a massage device.

17. The method of claim 1, wherein the conductive metal portion is a nanoplate, and wherein the nanoplate has a peak absorption wavelength in a range of 750 nm to 1200 nm.

18. The method of claim 1, wherein distributing the composition comprises distributing the composition with a low frequency ultrasound device.

19. The method of claim 7, wherein redistributing solution of unassembled plasmonic nanoparticles from the skin surface to a portion of the hair follicle comprises distribution with the mechanical vibration device, wherein the mechanical vibration device comprises at least one of a massage device and an ultrasound device configured for bubble formation or liquid micro streaming.

20. The method of claim 7, wherein the conductive metal portion is a nanoplate, and wherein the coating is less conductive than the conductive metal portion.

* * * * *